US012589114B2

(12) United States Patent
Zhu et al.

(10) Patent No.: US 12,589,114 B2
(45) Date of Patent: Mar. 31, 2026

(54) GABA AGONISTS AND ANTAGONISTS AFFECT DIFFERENTIATION OF HEMATOPOIETIC STEM CELLS AND MEGAKARYOCYTE PROGENITORS

(71) Applicant: The Board of Trustees of the Leland Stanford Junior University, Stanford, CA (US)

(72) Inventors: Fangfang Zhu, Emeryville, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 697 days.

(21) Appl. No.: 17/610,410

(22) PCT Filed: May 11, 2020

(86) PCT No.: PCT/US2020/032363
§ 371 (c)(1),
(2) Date: Nov. 10, 2021

(87) PCT Pub. No.: WO2020/231935
PCT Pub. Date: Nov. 19, 2020

(65) Prior Publication Data
US 2022/0218753 A1 Jul. 14, 2022

Related U.S. Application Data

(60) Provisional application No. 62/846,865, filed on May 13, 2019.

(51) Int. Cl.
| | |
|---|---|
| *A61K 35/18* | (2015.01) |
| *A61K 35/19* | (2015.01) |
| *C07K 14/475* | (2006.01) |
| *C07K 14/705* | (2006.01) |
| *C12N 15/113* | (2010.01) |
| *C12N 15/90* | (2006.01) |

(52) U.S. Cl.
CPC .............. *A61K 35/18* (2013.01); *A61K 35/19* (2013.01); *C07K 14/475* (2013.01); *C07K 14/705* (2013.01); *C12N 15/1138* (2013.01); *C12N 15/907* (2013.01); *C12N 2310/20* (2017.05); *C12N 2506/11* (2013.01); *C12N 2740/16043* (2013.01)

(58) Field of Classification Search
CPC ...... A61K 35/18; A61K 35/19; C07K 14/475; C07K 14/705; C12N 2310/20; C12N 15/1138; C12N 15/907; C12N 2506/11; C12N 2740/16043
See application file for complete search history.

(56) References Cited

U.S. PATENT DOCUMENTS

| | | | | |
|---|---|---|---|---|
| 5,463,054 A | * | 10/1995 | Thurkauf | C07D 487/14 544/251 |
| 2014/0205582 A1 | * | 7/2014 | Karsunky | A61K 35/19 435/372 |

FOREIGN PATENT DOCUMENTS

| | | | | |
|---|---|---|---|---|
| CN | 107922926 A | 4/2018 | | |
| WO | WO2016/191879 | 12/2016 | | |
| WO | WO-2017034459 A1 | * | 3/2017 | A61K 35/15 |

OTHER PUBLICATIONS

Duke RK, et. al. J Neurochem. Dec. 2000;75(6):2602-10 (Year: 2000).*

Cavagnini F, et. al. Acta Endocrinol (Copenh). Feb. 1980;93(2):149-54 (Year: 1980).*

Hanley MB, et. al. Stem Cells. Sep. 2005;23(8):1170-9 (Year: 2005).*

Merck Manual, (Feb. 12, 2018), Drug Administration. http://www.merckmanuals.com/home/drugs/administration-and-kinetics-of-drugs/drug-administration (Year: 2018).*

National Cancer Institute, (Apr. 23, 2018), NCI Dictionary of Cancer Terms. https://www.cancer.gov/publications/dictionaries/cancer-terms/def/hematopoietic-stem-cell (Year: 2018).*

Mayo Clinic (Jun. 8, 2023). "Immune thrombocytopenia." [https://www.mayoclinic.org/diseases-conditions/idiopathic-thrombocytopenia-purpura/symptoms-causes/syc-20352325]. Accessed Jan. 28, 2025 (Year: 2023).*

Cines, DB., et. al. Blood 106.7 (2005): 2244-2251 (Year: 2005).*

Tomer, A, et. al. (1987): 1735-1742 (Year: 1987).*

Steidl, Ulrich, et al. Blood 104.1 (2004): 81-88. (Year: 2004).*

Bormann, Joachim, et. al. Trends in neurosciences 18.12 (1995): 515-519. (Year: 1995).*

Nasreddine, Wassim, et. al. Epilepsia 49.3 (2008): 438-445 (Year: 2008).*

Petroff OA, et. al. Ann Neurol. Dec. 1996;40(6):908-11 (Year: 1996).*

Tichy E, et. al. J Pediatr Pharmacol Ther. Jan. 2003;8(1):29-33 (Year: 2003).*

Yamauchi, Tatsuhito, et. al. European Journal of Neuroscience 12.9 (2000): 3433-3436. (Year: 2000).*

(Continued)

*Primary Examiner* — Marcia S Noble
*Assistant Examiner* — Zanna Maria Beharry
(74) *Attorney, Agent, or Firm* — Pamela J. Sherwood; Bozicevic, Field & Francis LLP

(57) ABSTRACT

GABRR1 is shown to be expressed on subsets of hematopoietic stem cells (HSCs) and megakaryocyte progenitors (MkPs). Inhibition of GABRR1 inhibits MkP differentiation and reduction of platelet numbers in blood. Overexpression of GABRR1 or treatment with agonists significantly promotes MkP generation and growth of megakaryocytes.

7 Claims, 20 Drawing Sheets

(56) References Cited

OTHER PUBLICATIONS

Qian et al. (1998) "Molecular and Pharmacological Properties of GABA-rho Subunits from White Perch Retina", Journal of Neurobiology, vol. 37, No. 2, p. 3057320, Abstract.

Zangiacomi et al. (2009) "Human Cord Blood-Derived Hematopoietic and Neural-Like Stem/Progenitor Cells are Attracted by the Neurotransmitter GABA". Stem Cells and Development, vol. 18, No. 9, p. 1369-1377. Abstract; p1369, col. 1, para 1.

Zhu et al., (2018) "Screening for genes that regulate the differentiation of human megakaryocytic lineage cells". PNAS, vol. 115, No. 40, E93087E9316. Abstract; pE9312.

* cited by examiner

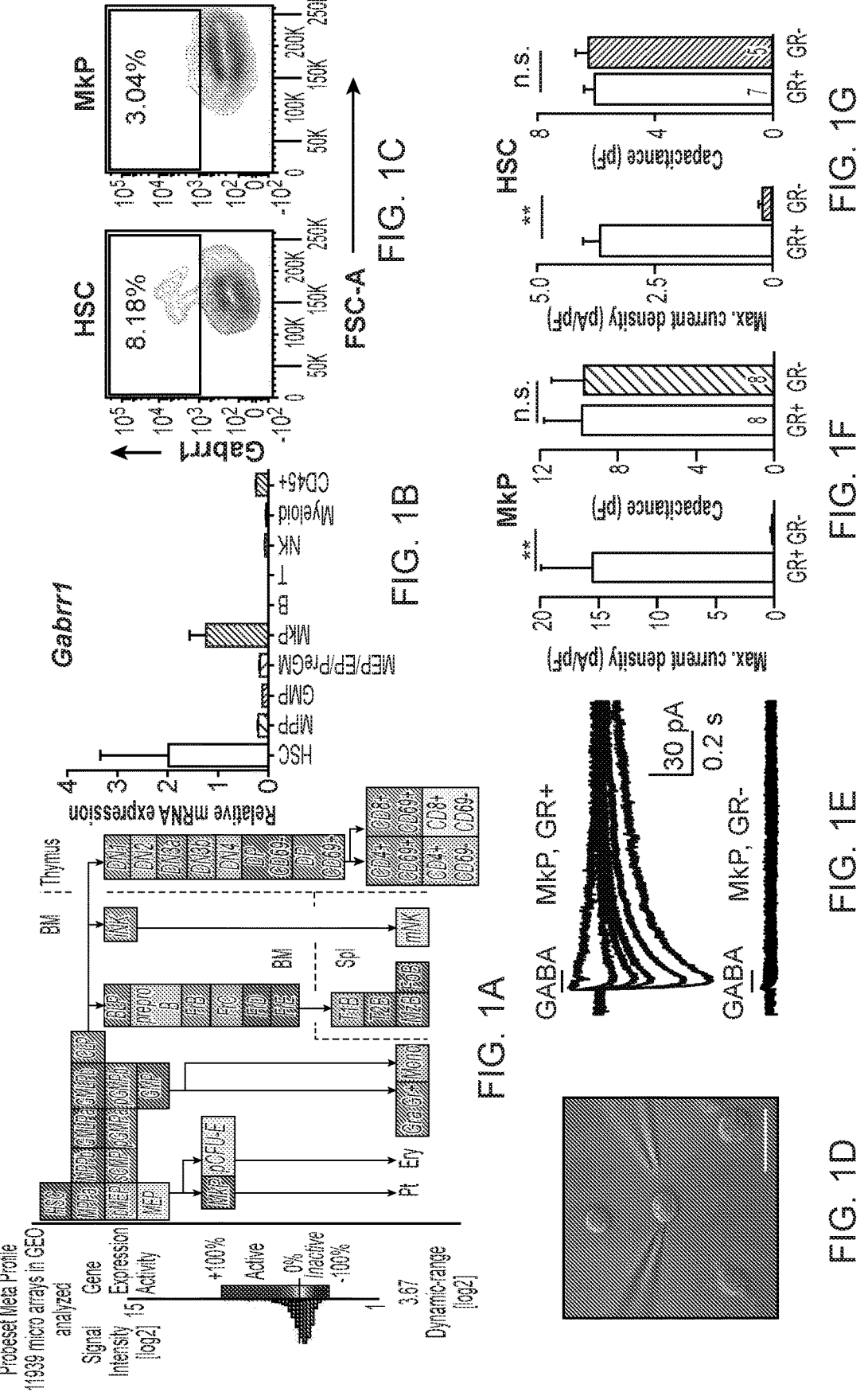

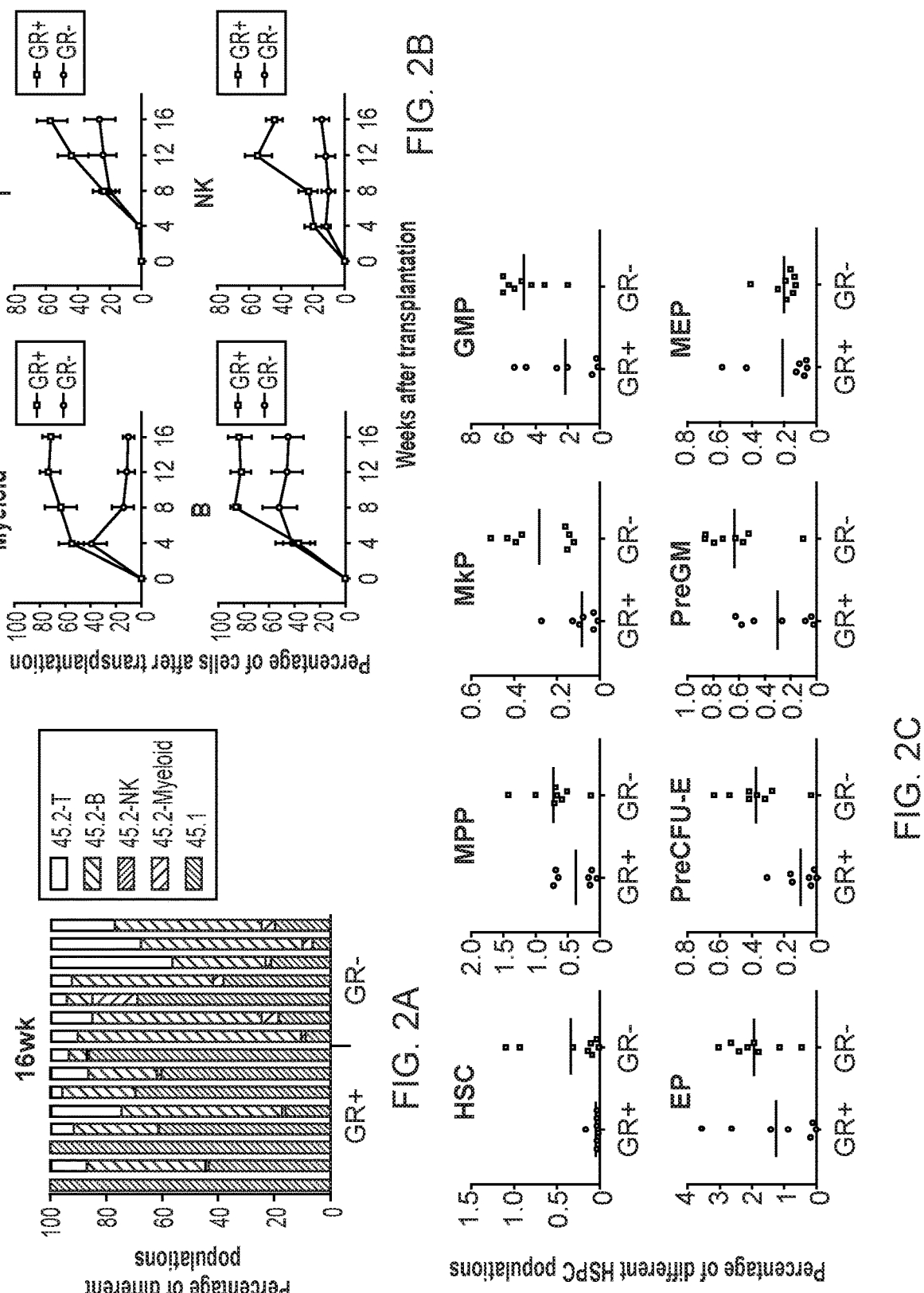

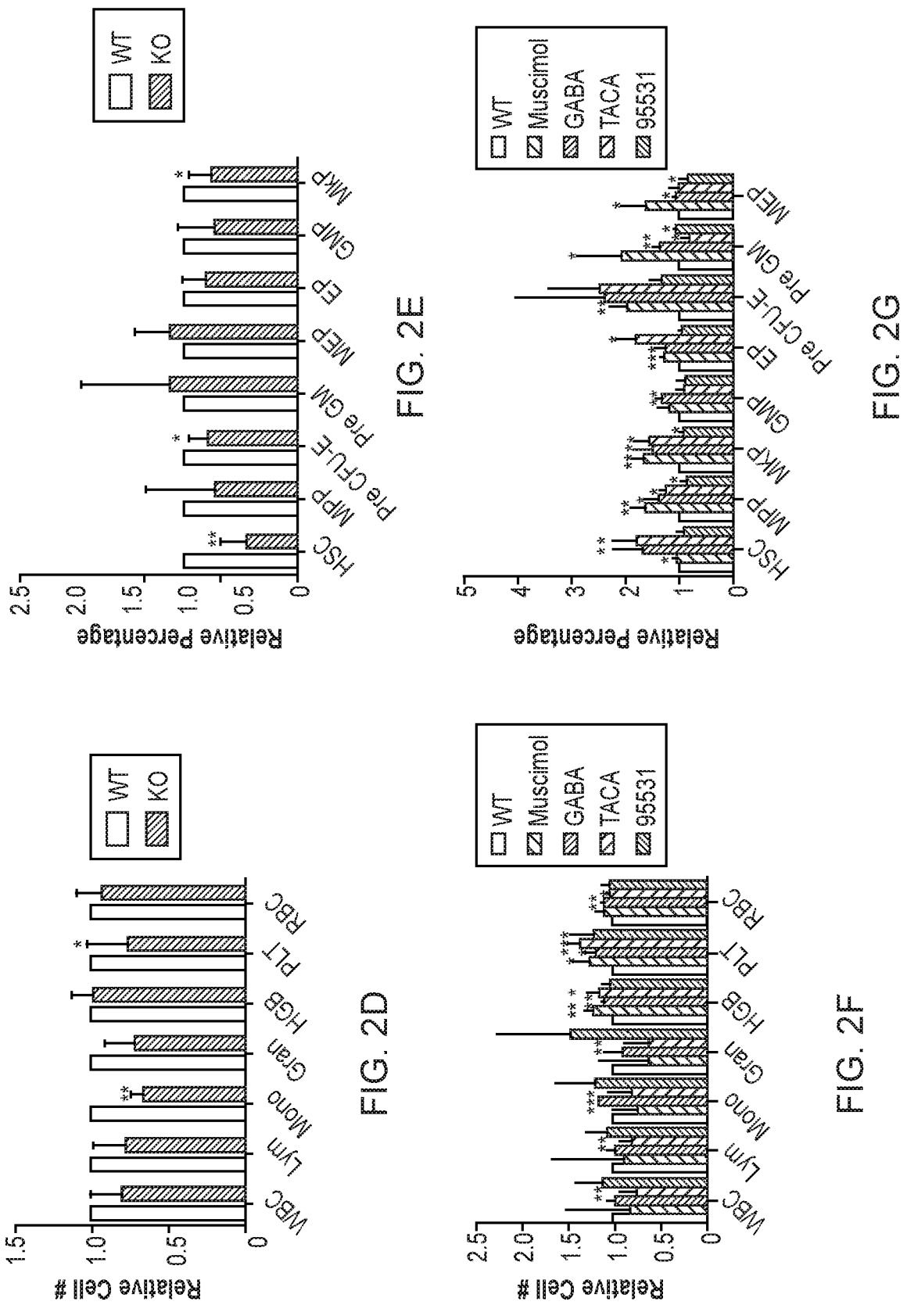

GABA AGONISTS AND ANTAGONISTS AFFECT DIFFERENTIATION OF HEMATOPOIETIC STEM CELLS AND MEGAKARYOCYTE PROGENITORS

CROSS REFERENCE

This application claims the benefit of PCT Application No. PCT/US2020/032363, filed May 11, 2020, which claims the benefit of U.S. Provisional Patent Application No. 62/846,865, filed May 13, 2019, which applications are incorporated herein by reference in their entirety.

BACKGROUND

γ-Aminobutyric acid (GABA) is the major inhibitory neurotransmitter in the vertebrate central nervous system and plays a role in neurogenesis. In addition, GABA is involved in various peripheral tissues and organs, such as the intestine, stomach et al. However, to date, the cell-type specific expression of GABA receptors, or their anatomical distribution and functional properties in hematopoietic stem and progenitor cells (HSPCs) has never been reported.

HSCs are capable of generating multiple different cell types in a stepwise way. Megakaryocyte-erythroid progenitors (MEPs), derived from HSCs, are bi-potent progenitors, which can differentiate into either MkPs (which give rise to platelets) or erythroid progenitors (EPs; which gives rise to erythrocytes). Supplementing MkPs is a promising strategy to overcome severe thrombocytopenia for rapid recovery of blood-clotting function in patients. Therefore, identification of the regulators that facilitate MkP generation and differentiation during hematopoiesis has become an important topic.

SUMMARY

Compositions and methods are provided for the modulation of megakaryopoiesis in vivo and in vitro. In some embodiments the methods provide for enhanced production of megakaryocytes and platelets from hematopoietic stem (HSC) and progenitor cells. Megakaryocyte-erythroid progenitors (MEPs), derived from HSCs, are bi-potent progenitors, which can differentiate into either megakaryocyte progenitors (MkPs), which give rise to platelets; or erythroid progenitors (EPs), which gives rise to erythrocytes. It is surprisingly found that MkP cells express the GABAρ receptor GABRR1, and respond to GABRR1 agonists by increasing production of MkP cells in bone marrow, or from progenitor cells in vitro.

In some embodiments a method is provided for enhancing production of one or more of MkP cells, megakaryocytes, and platelets, the method comprising contacting a cell population comprising hematopoietic stem (HSC) and progenitor cells with a dose of an agonist of GABRR1 effective to increase production of MkP cells, megakaryocytes, and/or platelets. In some embodiments the contacting is performed in vivo. In some such embodiments a subject suffering from thrombocytopenia, or predisposed to development of thrombocytopenia, is contacted with an effective dose and regimen of an agonist of GABRR1 to increase production of megakaryocytes and platelets derived therefrom. Following treatment the individual may be monitored for clinical indicia of thrombocytopenia.

In some embodiments an in vitro culture system for production of cells of the megakaryocyte lineage, e.g. MEPs, MkP, megakaryocytes, etc. is provided. The culture system comprises hematopoietic stem or progenitor cells capable of giving rise to cells of the megakaryocyte lineage, e.g. HSC, MEP, etc. in a culture medium comprising an effective concentration of a GABRR1 agonist.

Agonists of GABRR1 useful in the methods of the invention include, without limitation 4-aminobutanoic acid (GABA), trans-4-aminocrotonic acid (TACA), and muscimol. In some embodiments the agonist is selective for a GABA rho receptor, e.g. GABRR1 such as TACA; cis-4-amino-crotonic acid (CACA), (+)-cis-2-(aminomethyl)cyclopropane carboxylic acid (CAMP); (±)-trans-2-(aminomethyl) cyclopropane carboxylic acid (TAMP); trans-2-methyl-4-aminocrotonic acid (2-MeTACA); 3-(aminomethyl)-1-oxo-1-hydroxy-phospholane (3-AMOHP); 3-(amino)-1-oxo-1-hydroxy-phospholane (3-AOHP); 3-(guanidino)-1-oxo-1-hydroxy-phospholane (3-GOHP); 4-aminocyclopent-1-enecarboxamide (4-ACPAM); 4-amino-N-hydroxycyclopent-1-enecarboxamide (4-ACPHA), and the like.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1K. FIG. 1A Gabrr1 expression and function in mouse hematopoietic system. Expression of Gabrr1 in different mouse hematopoietic populations in Gene Expression Commons, FIG. 1B Gene expression analysis of Gabrr1 in different mouse HSPC populations by real time PCR. Data shown are mean±SD from three replicates of the same group, and are representative of at least three independent experiments. FIG. 1C Gabrr1 expression analysis in mouse HSPCs from bone marrow by multicolor flow cytometry. Numbers represent the percentage of Gabrr1+ cells, Data shown are representative of n=6 mice. FIG. 1D A representative image of a GR+ MkP for patch-clamp recording of GABA-evoked currents. FIG. 1E The representative current traces induced by application of 1 mM GABA in GR+ and GR− MkPs held at various membrane potentials from −80 mV at a step of 20 mV. FIG. 1F-1G. Summary graph of the maximum current density and cell capacitance of GR+ and GR− MkPs (F), and GR+ and GR− HSCs FIG. 1G-1H The I-V curves of peak current densities of GR+ MkPs and GR+ HSCs (the x-axis shows the holding voltages; the y-axis shows the current densities (peak current/cell capacitance)). FIG. 1I. Immunostaining analysis shows expression of GAD65+GAD67, GABA, vGAT, H2 and Synaptophysin (SP4) in the growth plate/epiphysis. J). Mice sections in different sites stained with pentachrome. FIG. 1K. The HSC and MkP associated genes were analyzed in purified mouse GR+ and GR− HSCs and MkPs by real-time PCR, Data shown in FIGS. 1F and 1G are mean±SEM. Number of cells analyzed are indicated in the bars. **P<0.01. Scale bar, 20

Figures 1H, 1I, 1J, 1K:
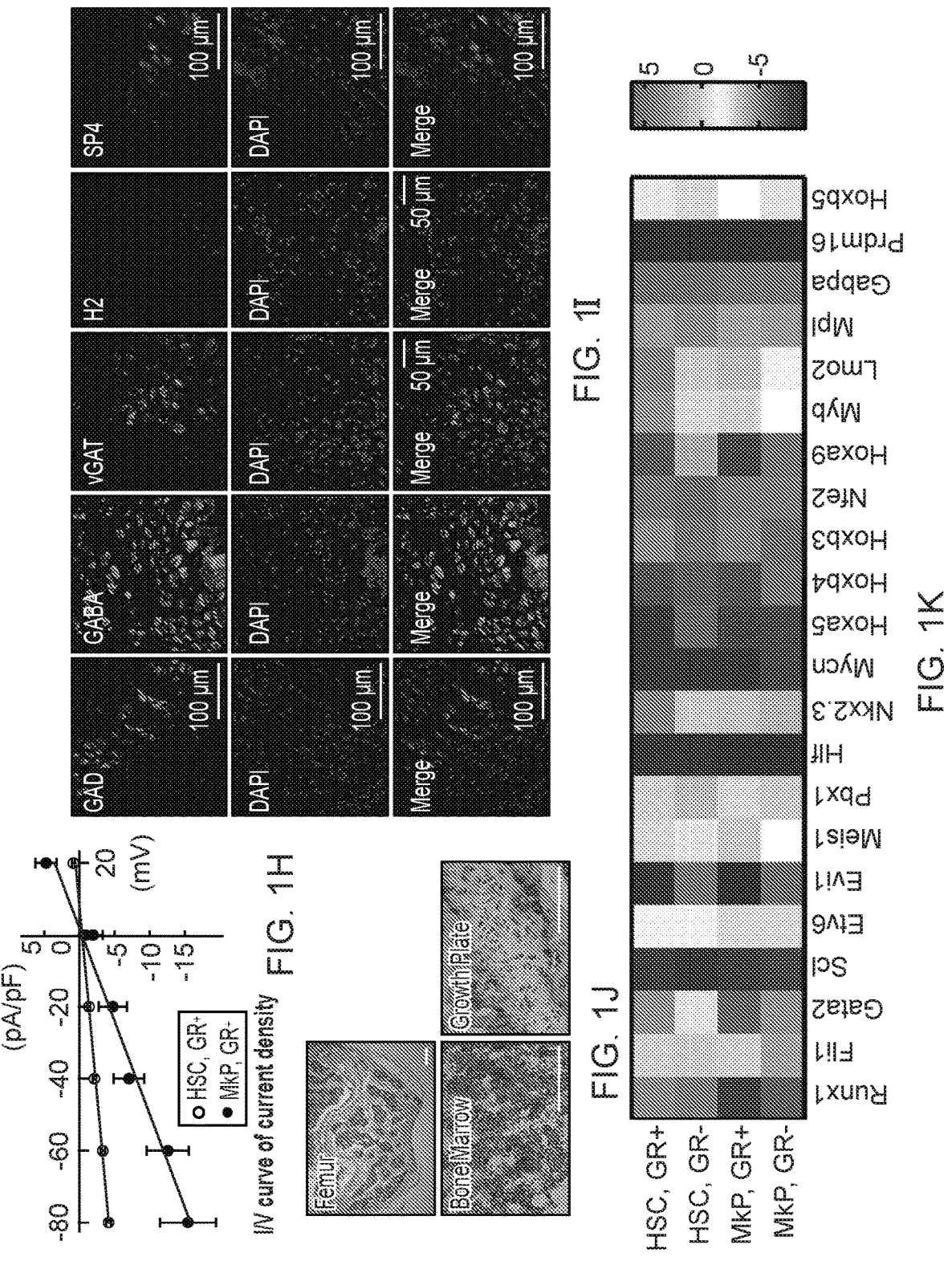

μM FIG. 1D, 50 μM (I middle panels) 100 μM (FIG. 1I left and right panels and FIG. 1J. lower panel), 200 μM (J upper panel).

FIG. 2A-2G. The effects of activation or inactivation of Gabrr1 on HSPC differentiation in mouse. FIG. 2A Percentage of chimerism at 16 weeks after transplanting GR+ HSCs (n=8 mice), or GR− HSCs (n=7 mice) into primary recipients. Each column represents an individual mouse. FIG. 2B Average donor lineage contributions of myeloid cells, B cells, T cells and NK cells in primary transplants. Error bars denote S.D. FIG. 2C Frequencies of HSPC populations from donor mice contributed in recipients. FIG. 2D The complete blood cell counts in peripheral blood of B6; 129S4-Gabrr1$^{tm1Llu}$/J mice and its approximate control WT B6129SF2/J mice. For each cell count, the number from the WT mice was set to 1, and the number from Gabrr1 KO mice was normalized to that. FIG. 2E The blood cell counts in peripheral blood of mice treated with agonists or antagonists of Gabrr1. RBC, white blood cell; Mono, monocyte; HGB, hemoglobin; Gran, granulocyte; Lym, lymphocyte; Plt, platelets; RBC, red blood cell. For each cell count, the number from the WT mice was set to 1, and the number from mice by other treatments was normalized to that. FIG. 2F, 2G Summary of mouse HSPCs from bone marrow of mice treated with agonists or antagonists of Gabrr1. For each HSPC population, the number from the WT mice was set to 1, and the number from mice by other treatments was normalized to that. Data shown in FIGS. 2D, 2E and 2F are mean±SD of individual mice groups (n=6 for each group) within the same experiment. *P<0.05, P<0.01, *P<0.001.

Figures 3A, 3B, 3C:
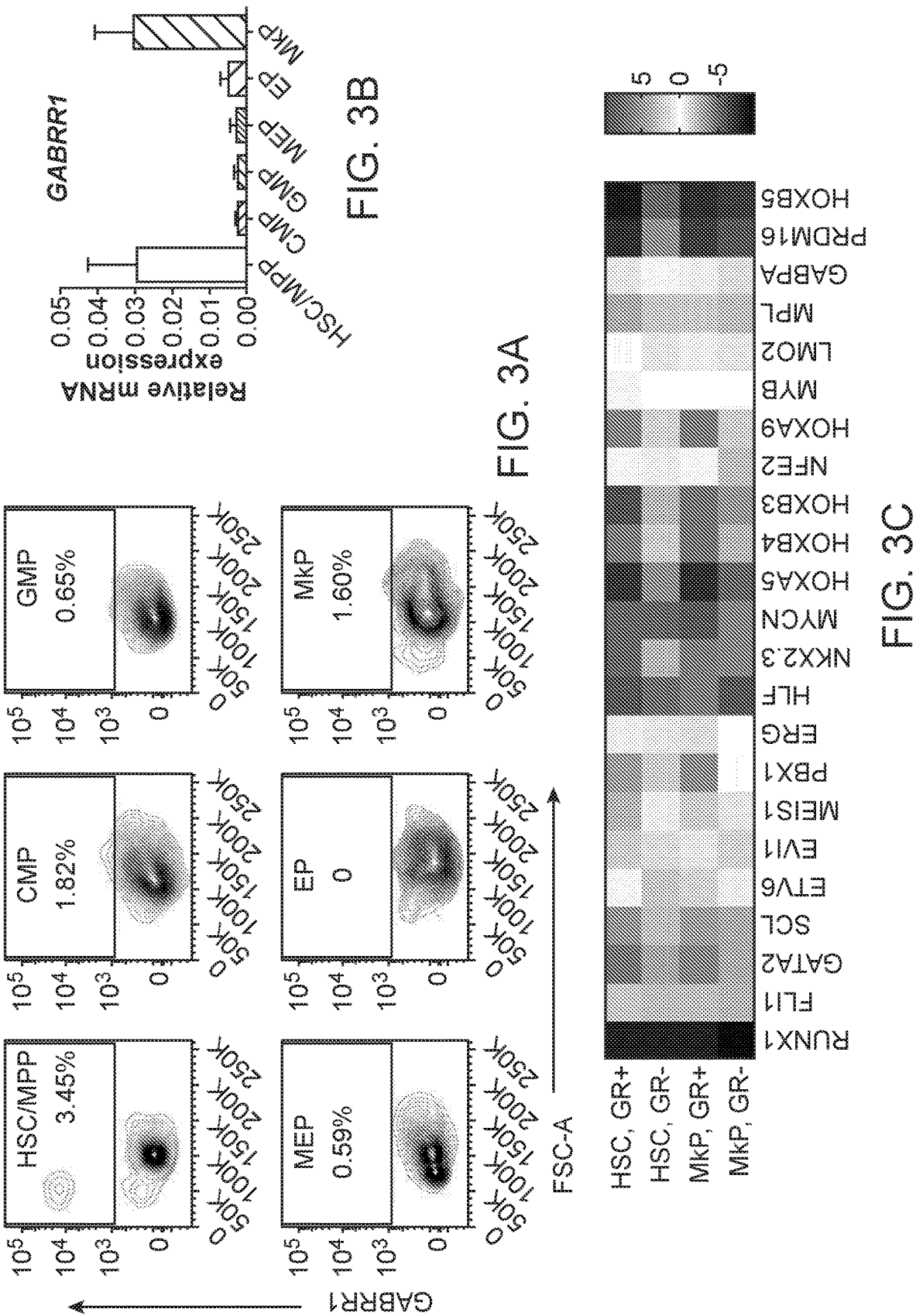
Figures 3D, 3E, 3F, 3G, 3H:
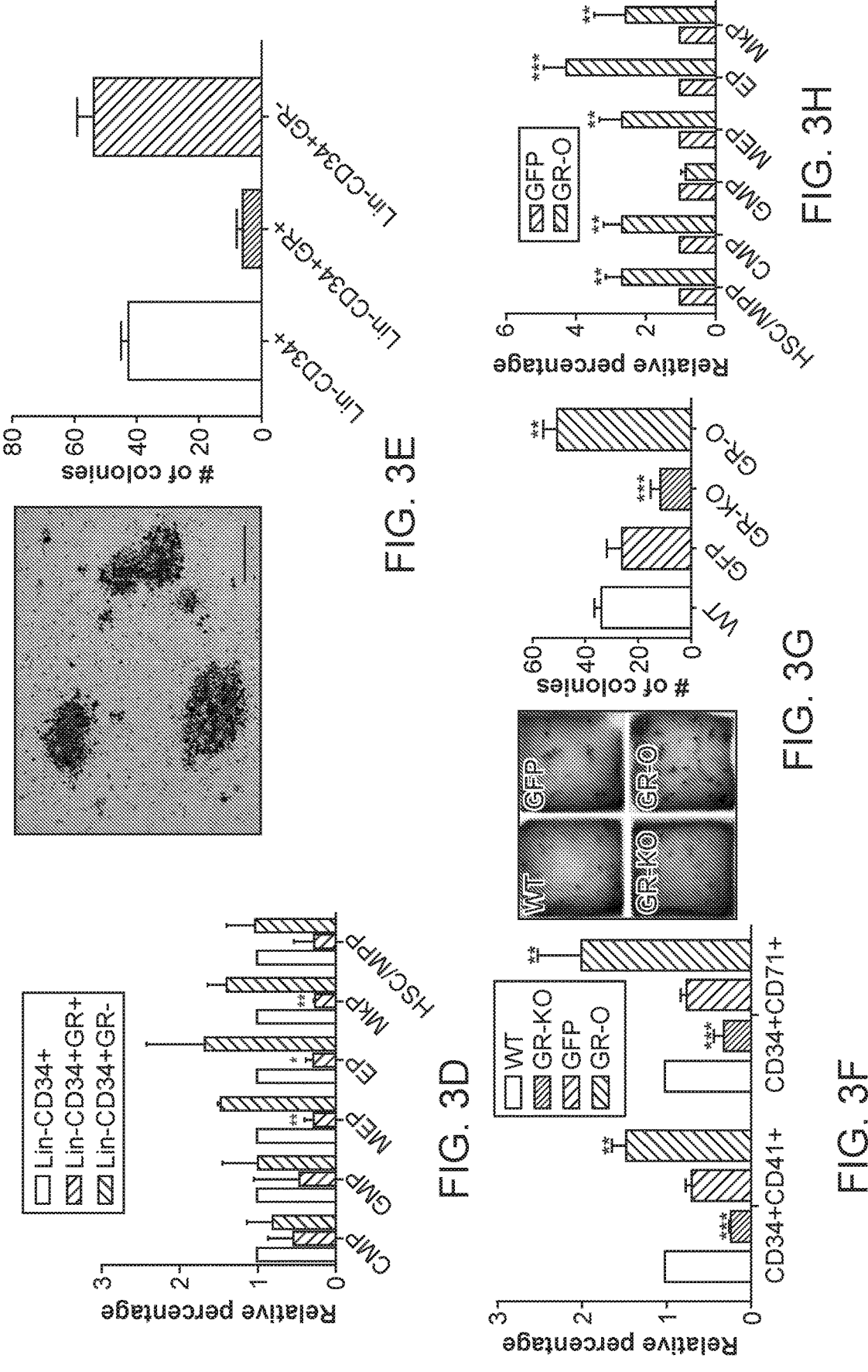

FIG. 3A-3H. GABRR1 expression and the consequence of GABRR1 ablation or overexpression in human hematopoietic system. FIG. 3A GABRR1 expression analysis in human HSPCs from bone marrow by multicolor flow cytometry. Numbers represent the percentage of GABRR1+ cells, FIG. 3B Expression of GABRR1 in human HSPC populations by real time PCR analysis. Data shown are mean±SD. FIG. 3C The HSC and MkP associated genes were analyzed in purified GR+ HSCs, GR− HSCs, GR+ MkPs and GR− MkPs by real-time PCR. FIG. 3D Flow cytometry analysis of the HPSC subpopulations after differentiation in vitro from human Lin-CD34+, Lin-CD34+GR+, Lin-CD34+GR− cells. FIG. 3E CFU-MK colonies generated from Lin-CD34+, Lin-CD34+GR+ or Lin-CD34+GR− cells. FIG. 3F The changes of CD34+CD41+ cells (MkP) and CD34+ CD71+ cells (EP) after 7 days of differentiation from purified CD34+ cells with GABRR1 knockout or overexpression. The percentage of each HSPC population from the non-treated WT cells was set to 1, and the percentage from other treatments was normalized to that. FIG. 3G CFU-MK colonies generated from CD34+ bone marrow cells with GABRR1 knockout or overexpression. GR-KO, GABRR1 knockout; GR-O, GABRR1 overexpression. FIG. 3H Quantification of human HSPC subpopulation changes by multicolor flow cytometry, after 7 days of differentiation from bone marrow CD34+ cells with GABRR1 overexpression. The percentage of each HSPC population from the non-treated cells was set to 1, and the percentage from GABRR1-overexpressing cells was normalized to that. Data shown are representative of at least three independent experiments. Error bars indicate SD. *P<0.05, P<0.01, *P<0.001.

Figures 4A, 4B:
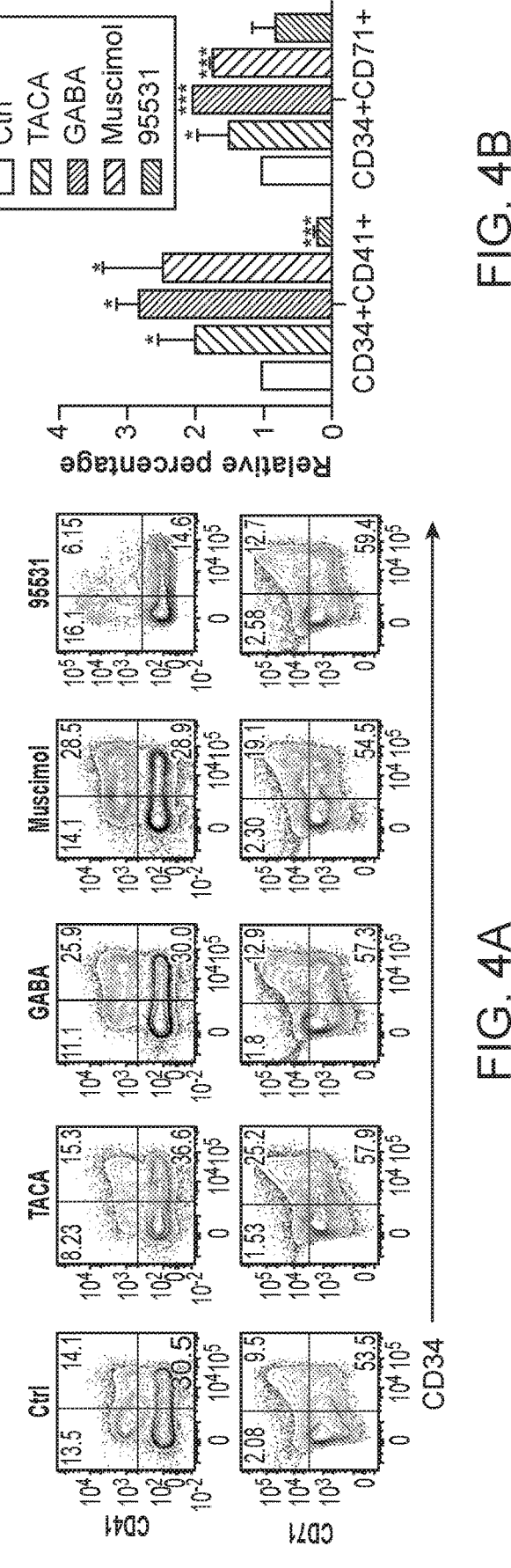
Figure 4C:
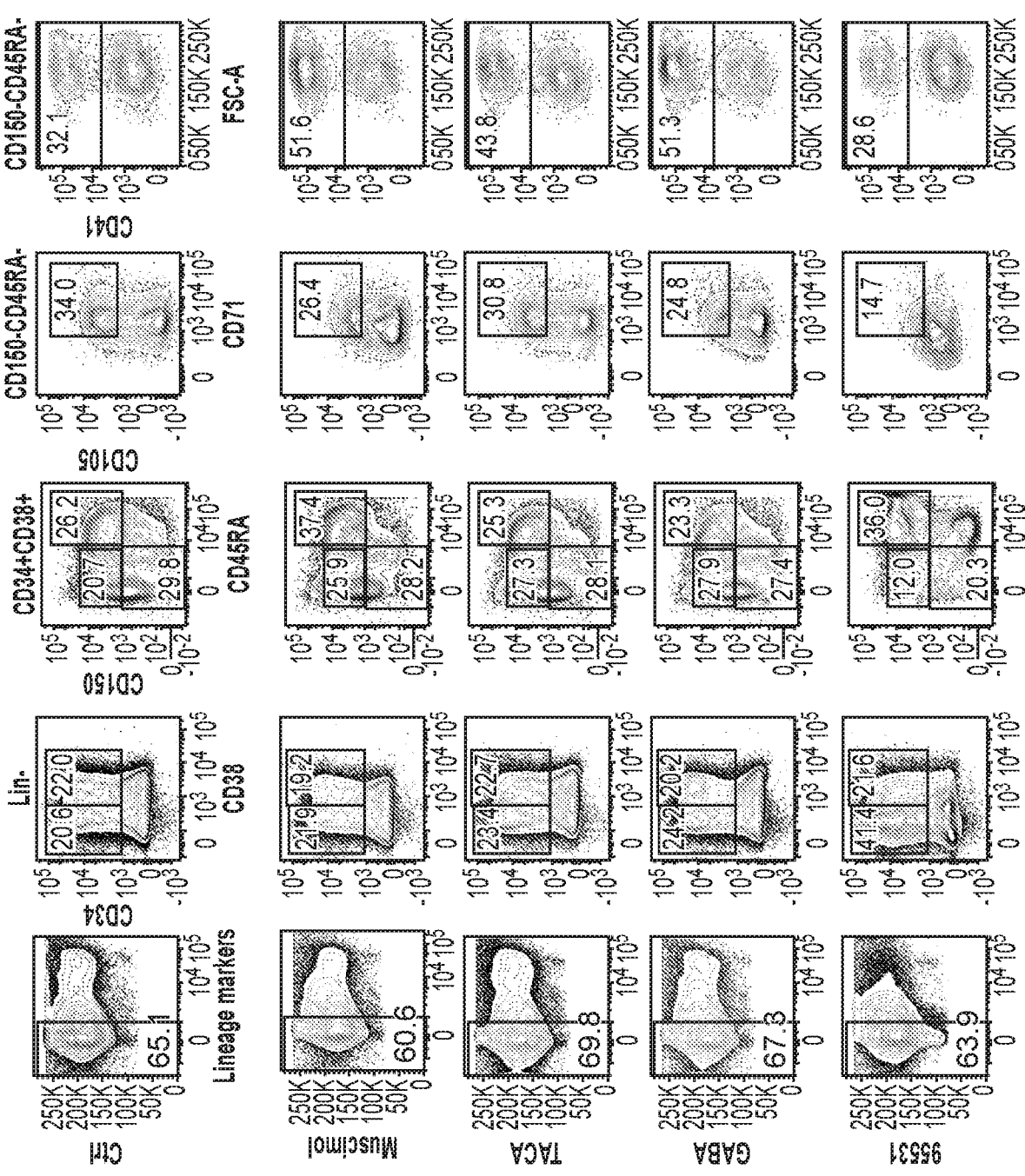
Figure 4E:
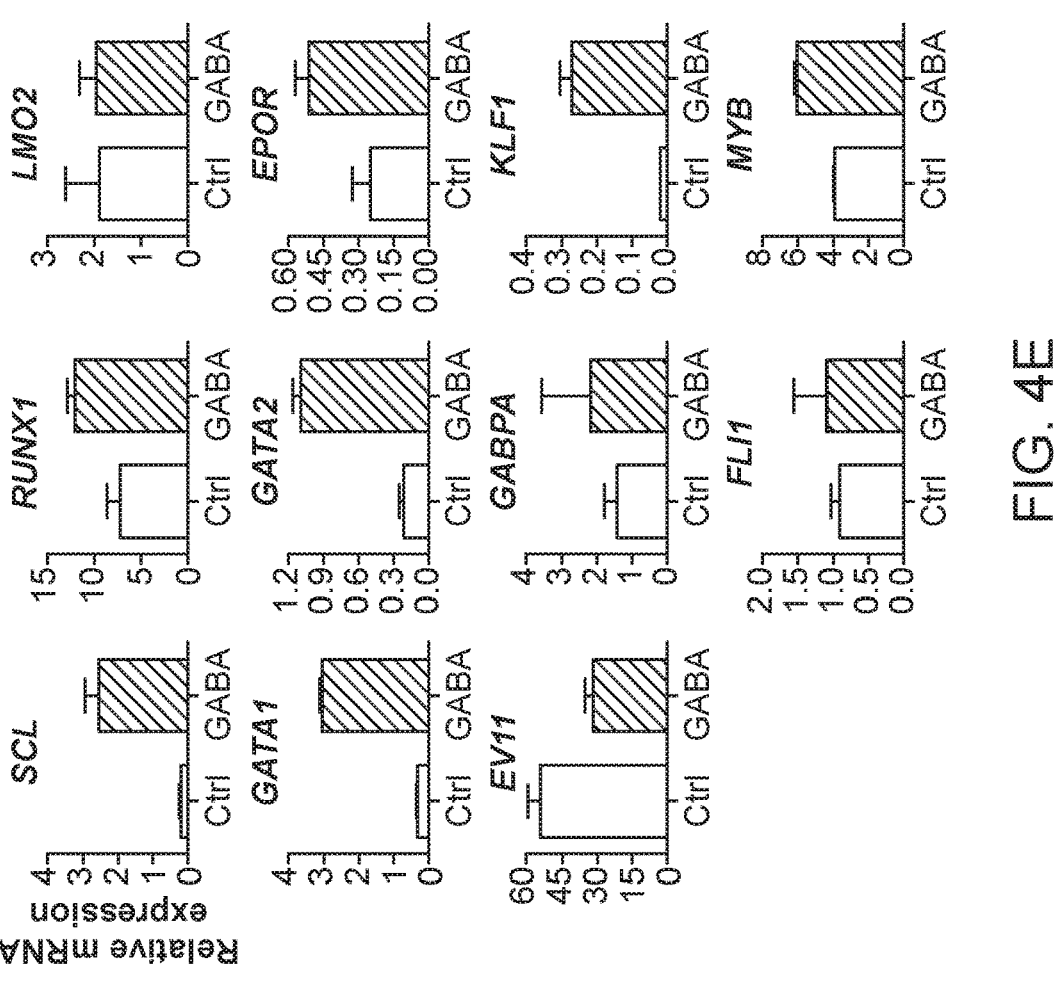
Figure 4D:
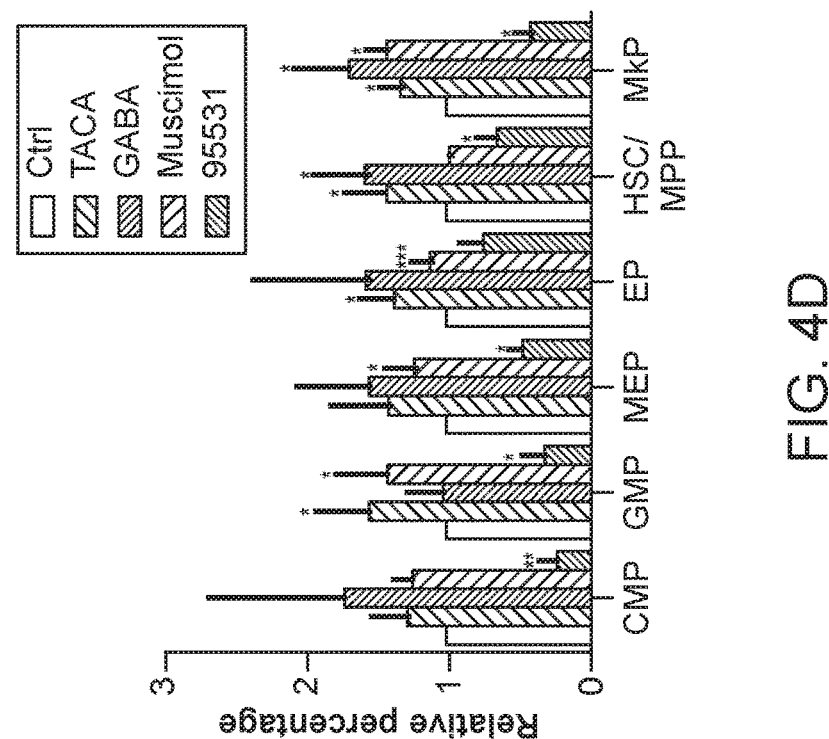
Figure 4F:
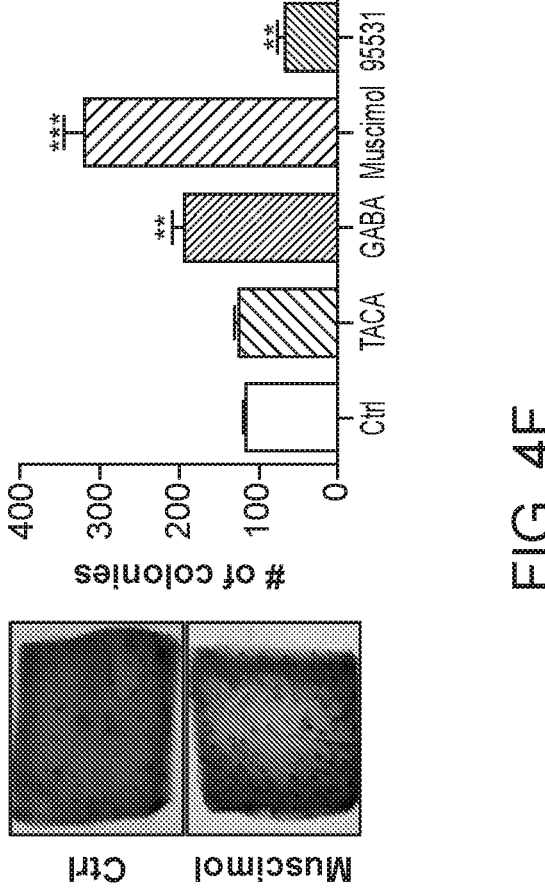

FIG. 4A-4F. The effects of GABRR1 agonists and antagonists on human HSPC differentiation. FIG. 4A Flow cytometry analysis of CD34+CD41+ (MkP) and CD34+CD71+ (EP) percentage in 7-day differentiated CD34+ cells treated with agonists or antagonists of GABRR1, FIG. 4B Quantification of CD34+CD41+ (MkP) and CD34+CD71+ (EP) percentage in 7-day differentiated CD34+ cells treated with agonists or antagonists of GABRR1. The percentage of each HSPC population from the non-treated cells was set to 1, and the percentage from other treatments was normalized to that. FIG. 4C-4D). Flow cytometry FIG. 4C and Quantification FIG. 4D of human HSPC subpopulation changes by multicolor flow cytometry after 7 days of differentiation from CD34+ bone marrow cells treated with agonists or antagonists of GABRR1. The percentage of each HSPC population from the non-treated cells was set to 1, and the percentage from other treatments was normalized to that. FIG. 4E Gene expression analysis of megakaryocytic and/or erythroid cells-associated genes by real time PCR in 7-day differentiated cells from CD34+ bone marrow cells treated with GABA. FIG. 4F CFU-Mk colonies generated from CD34+ bone marrow cells treated with agonists or antagonists of GABRR1. Data shown in FIGS. 4B, 4D, 4E and 4F are mean±SD from at least three independent experiments *P<0.05, P<0.01, *P<0.001.

Figure 5A:
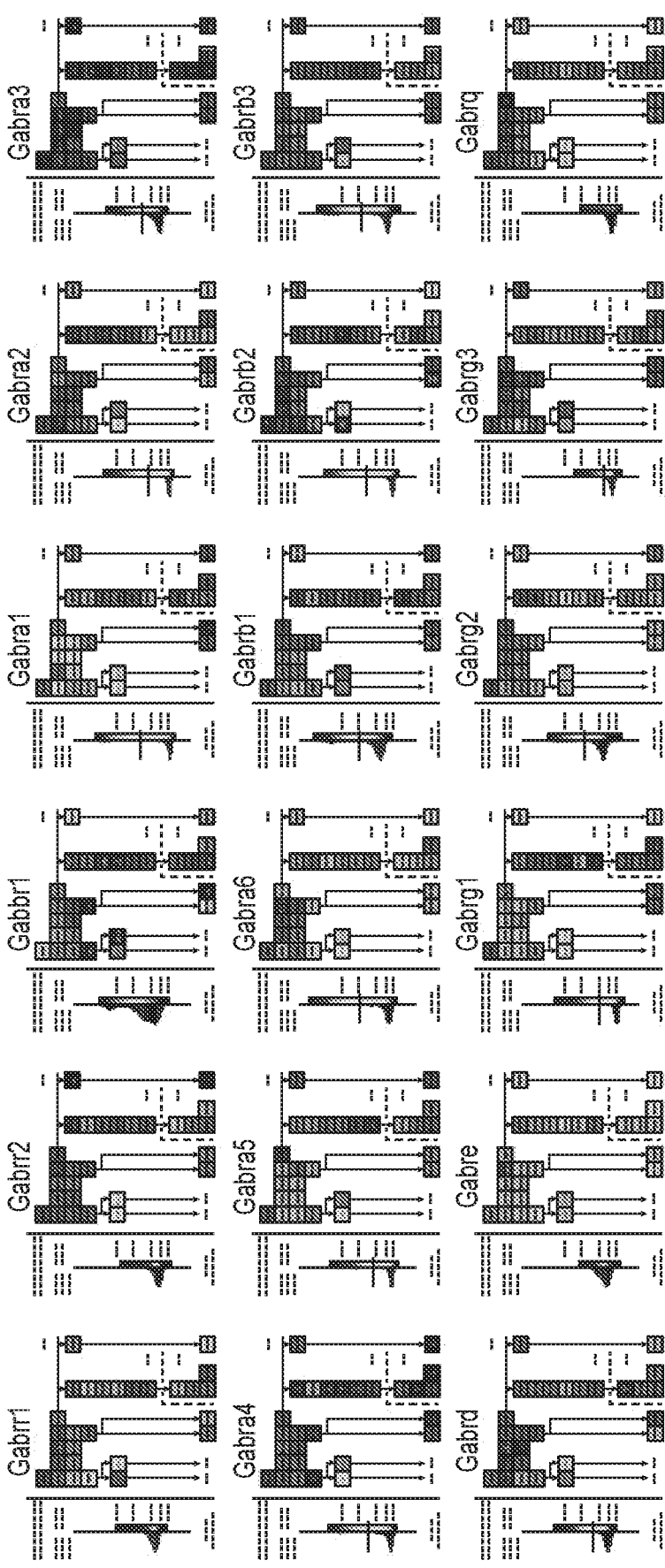
Figures 5B, 5C, 5D:
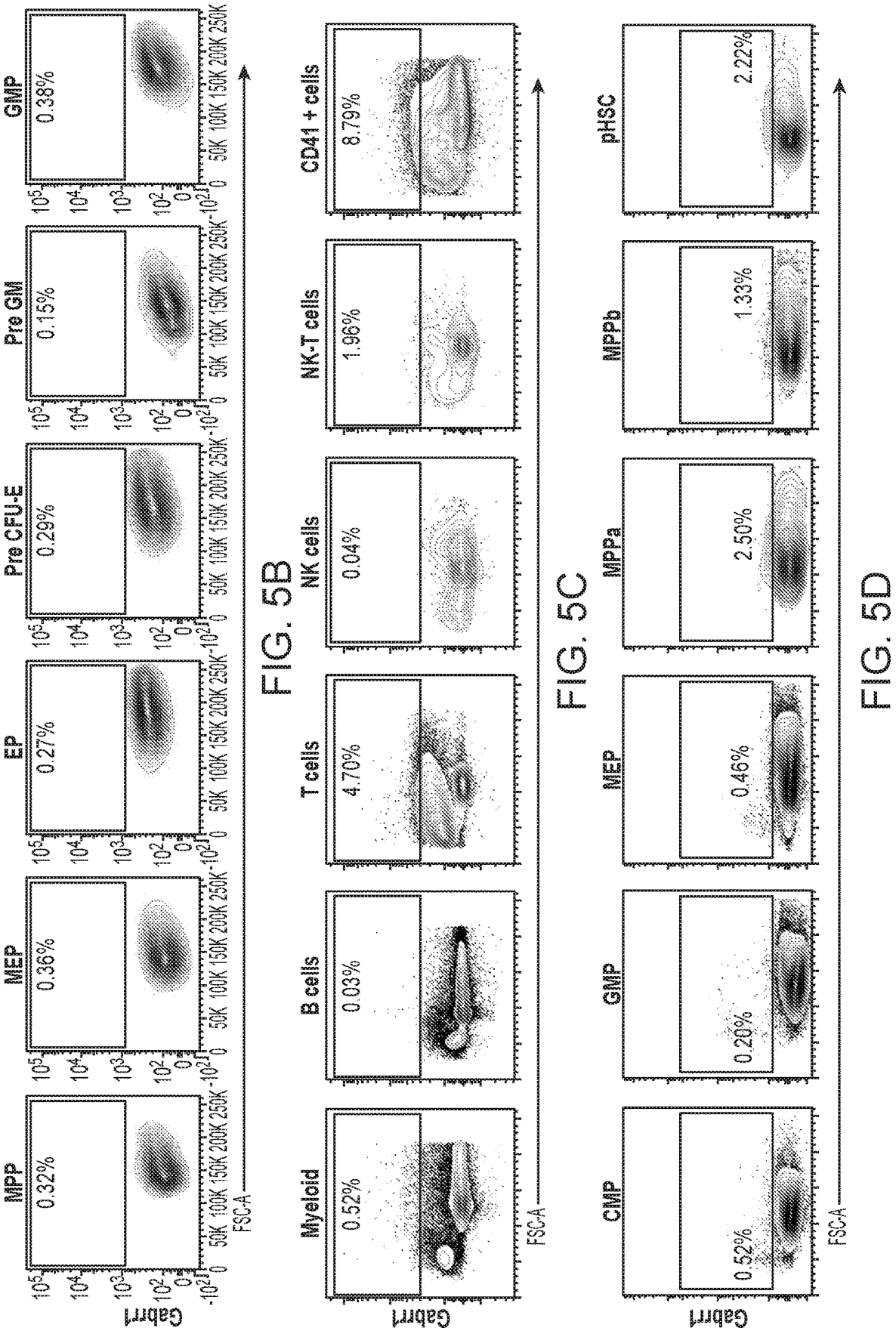
Figures 5E, 5F, 5G:
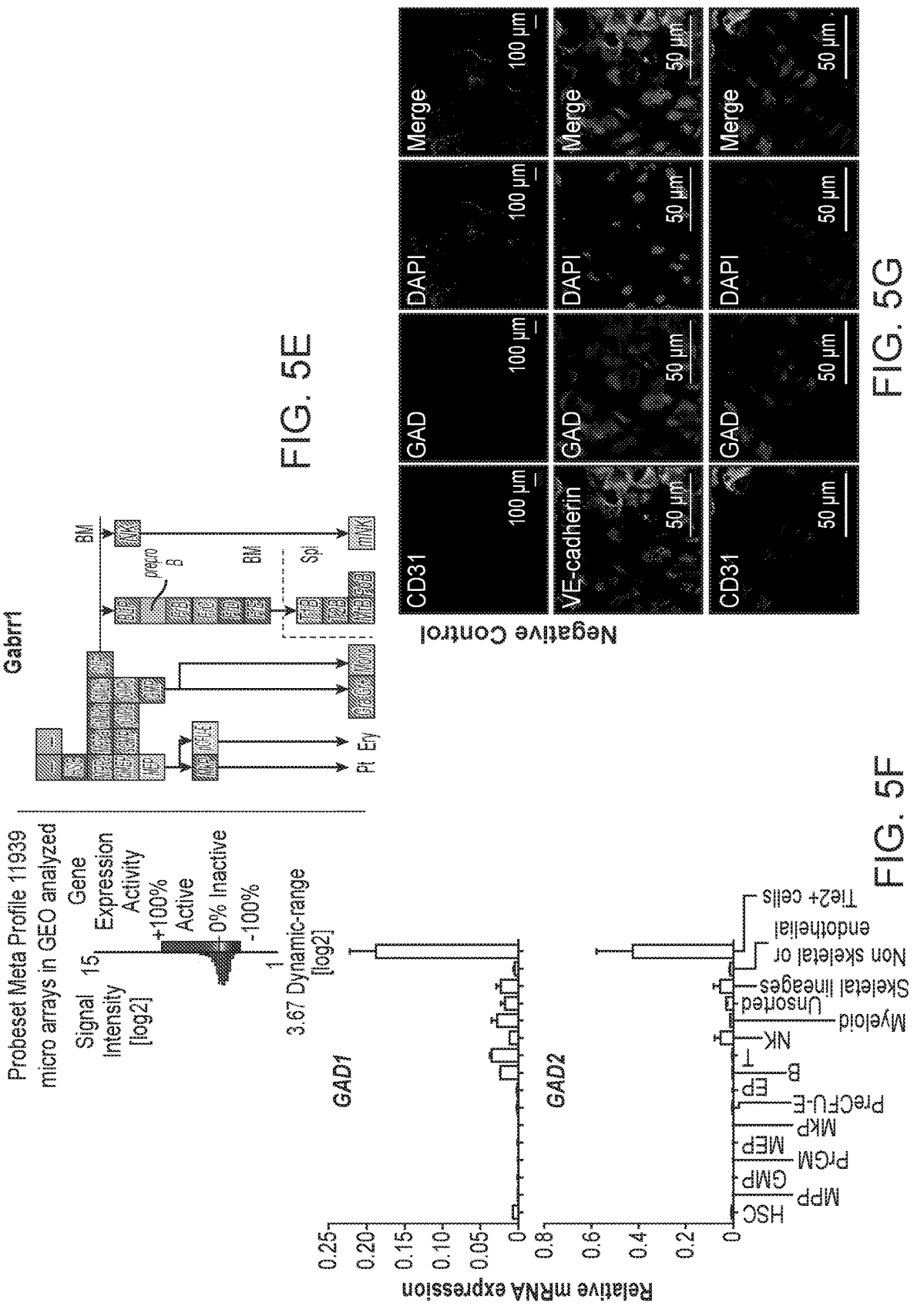

FIG. 5A-5G. FIG. 5A GEXC analysis showed the gene expression pattern of family members of GABA receptors in mouse hematopoietic cells in pooled microarray data. FIG. 5B Gabrr1 expression analysis in mouse HSPCs from bone marrow mononuclear cells (related to FIG. 10). FIG. 5C. Gabrr1 expression analysis in different mature blood cells. FIG. 5D Gabrr1 expression in immuno-phenotypically defined HSCs (pHSCs), MPPa and MPPb and other HSPC populations. Data are representative of n=6 mice. FIG. 5E GEXC analysis showed the gene expression pattern of Gabrr1 in microarray data reported by Sanjuan-Pla et al., 2013. FIG. 5F GAD1 and GAD2 expression in different hematopoietic and niche cell populations by real time PCR analysis. Data were presented as mean±SD from three replicates of the same group and are representative of three independent experiments FIG. 5G Immunostaining for the coexpression of endothelial markers (CD31 and VE-Cadherin) and GADs. Top panel is negative control, which showed staining with secondary antibodies only. Scale bar, 50 μM.

Figures 6A, 6B, 6C, 6D, 6E:
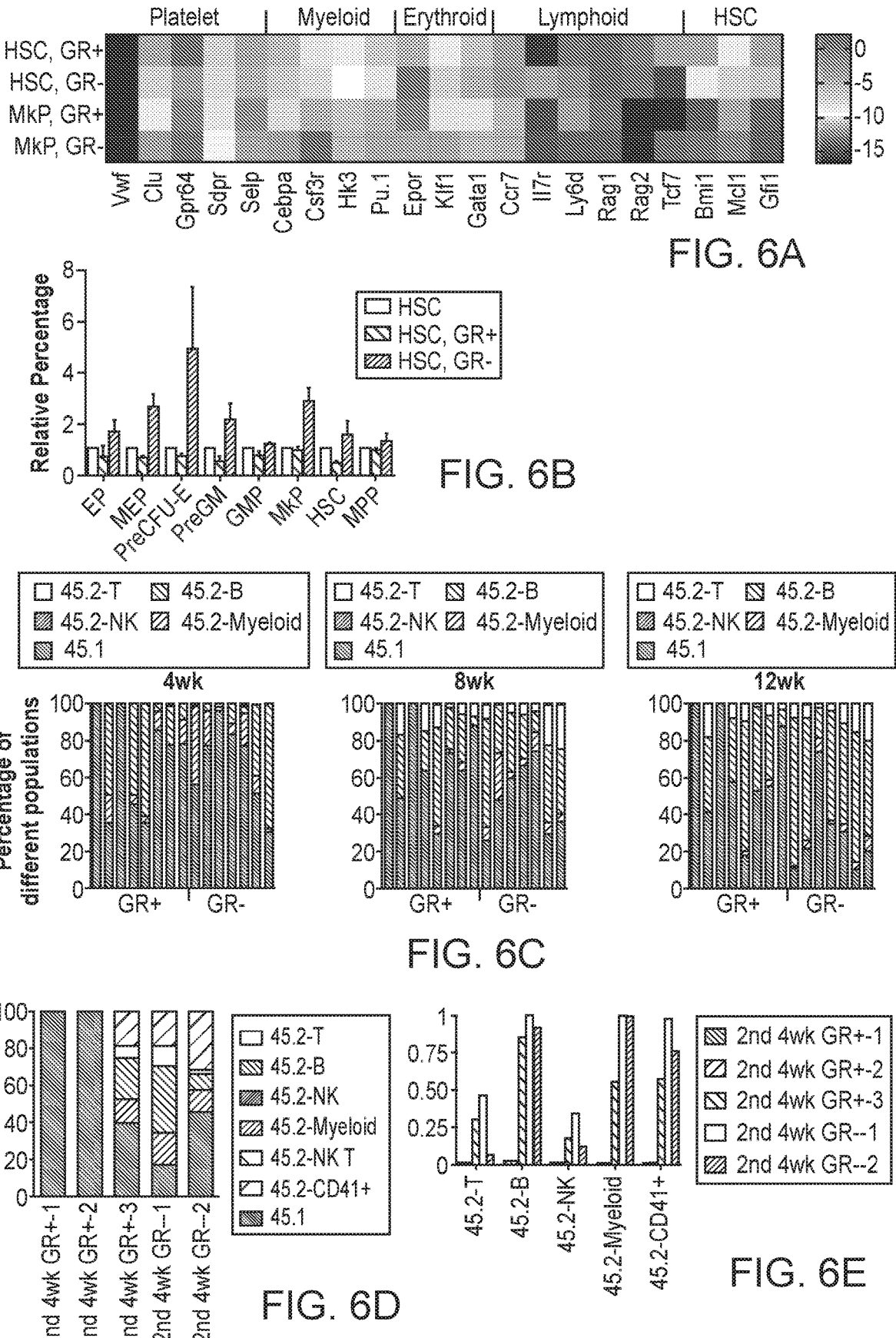

FIG. 6A-6E. FIG. 6A Expression analysis of the hematopoietic lineages associated genes in purified mouse GR+ HSCs, GR− HSCs, GR+ MkPs and GR− MkPs by real-time PCR. Numbers indicate ΔCt values to the housekeeping gene beta-actin. FIG. 6B Flow cytometry analysis of the HSPC subpopulations after differentiation in vitro from mouse GR+ HSCs and GR− HSCs, Data shown are mean±SD from three individual samples of the same group and are representative of at least three independent experiments. FIG. 6C Percentage of chimerism at 4, 8 and 12 weeks after transplanting GR+ HSCs (n=8 mice), or GR− HSCs (n=7 mice) into primary recipients. FIG. 6D-6E. Multilineage reconstitution after secondary transplantation confirms the HSC identity of the purified cells, Each column represents an individual mouse.

Figure 7A:
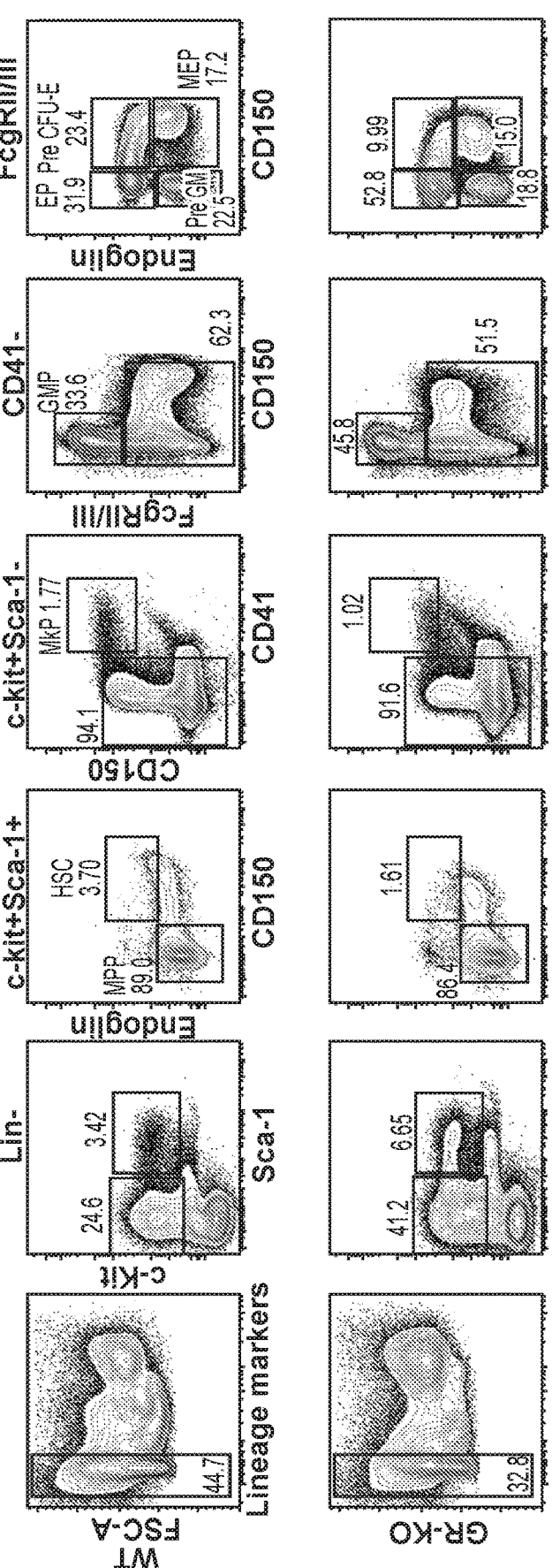
Figure 7B:
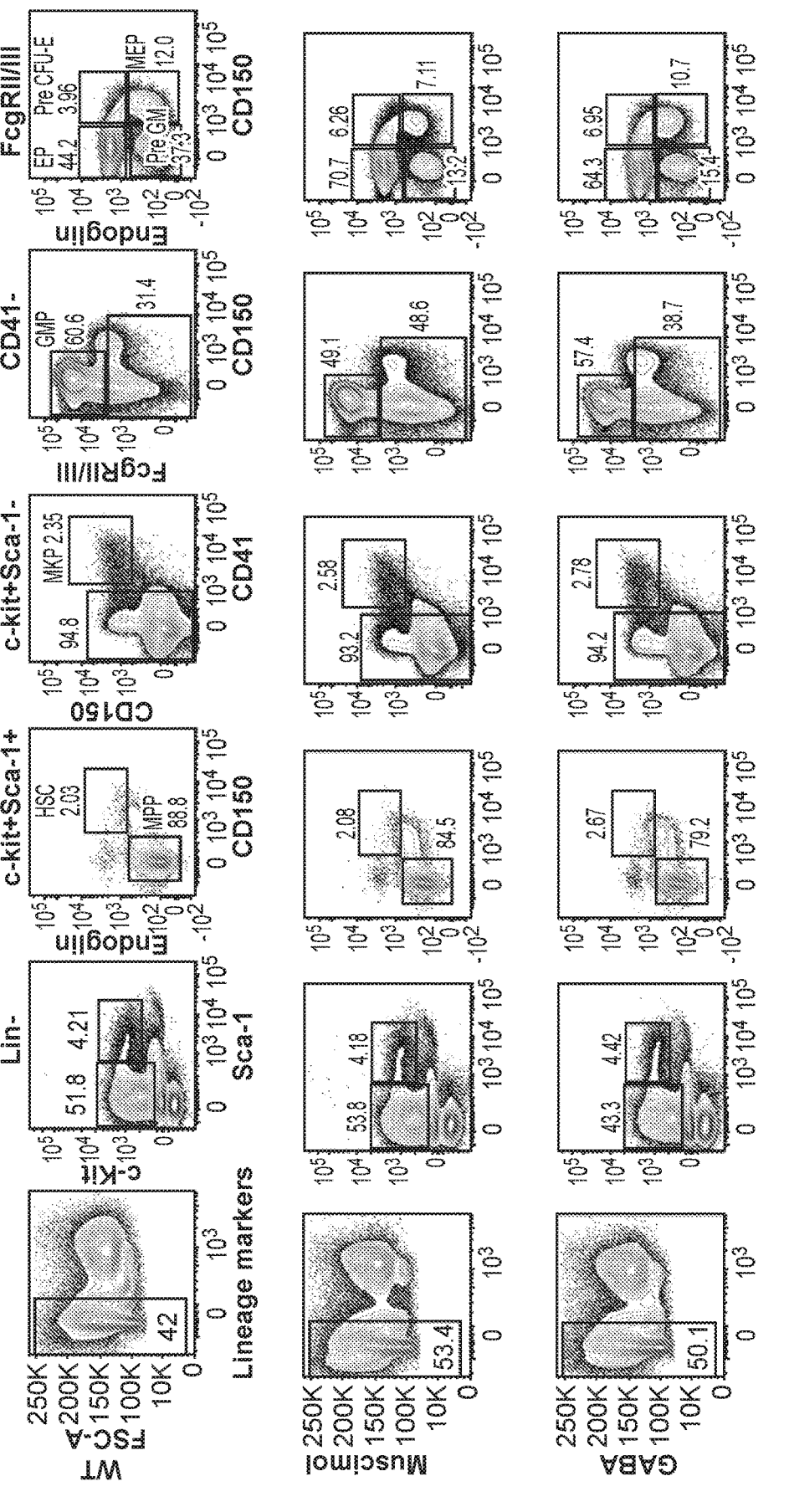
Figure 7B:
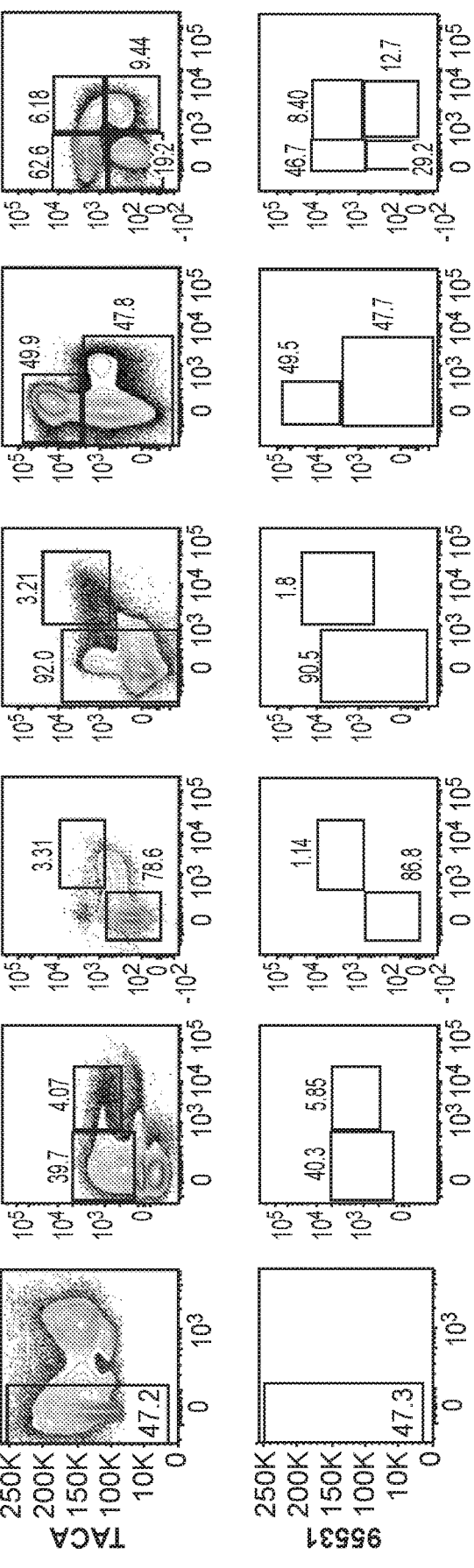

FIG. 7A-7B. FIG. 7A Multicolor flow cytometry analysis of HSPC population changes in B6; 129S4-Gabrr1$^{tm1Llu}$/J mice (bottom panel) and its approximate control B6129SF2/J (top panel). FIG. 7B Flow cytometry of bone marrow HSPC subpopulation changes by multicolor flow cytometry in mice treated with agonists or antagonists of Gabrr1.

Figures 8A, 8B:
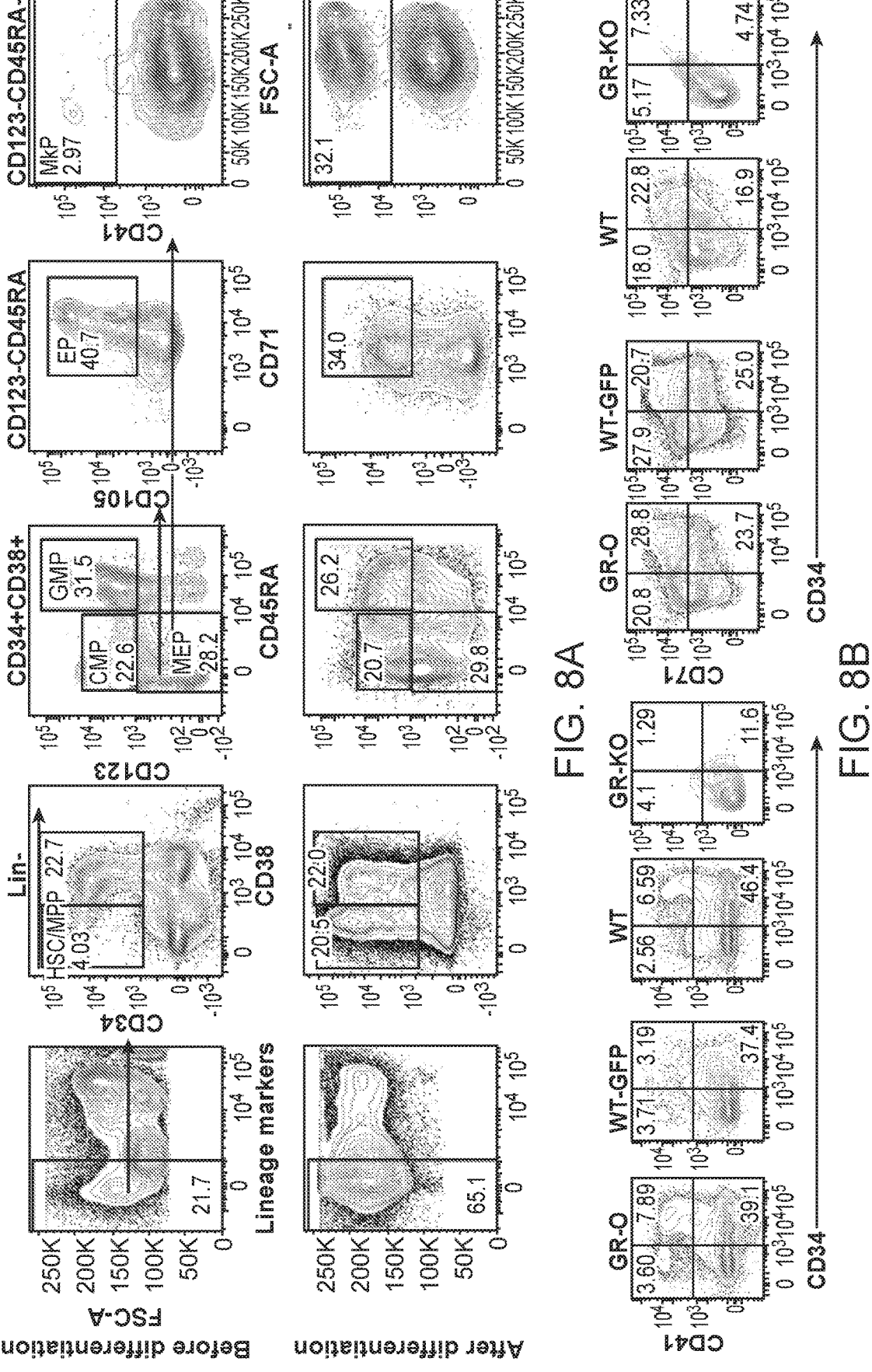

FIG. 8A-8E. FIG. 8A Gating strategy of human HSPCs subpopulations in multicolor flow cytometry and the HSPC population changes before and after 7 days of differentiation. Data are representative of at least three independent experiments. FIG. 8B Flow cytometry analysis of CD34+CD41+

Figures 8C, 8D:
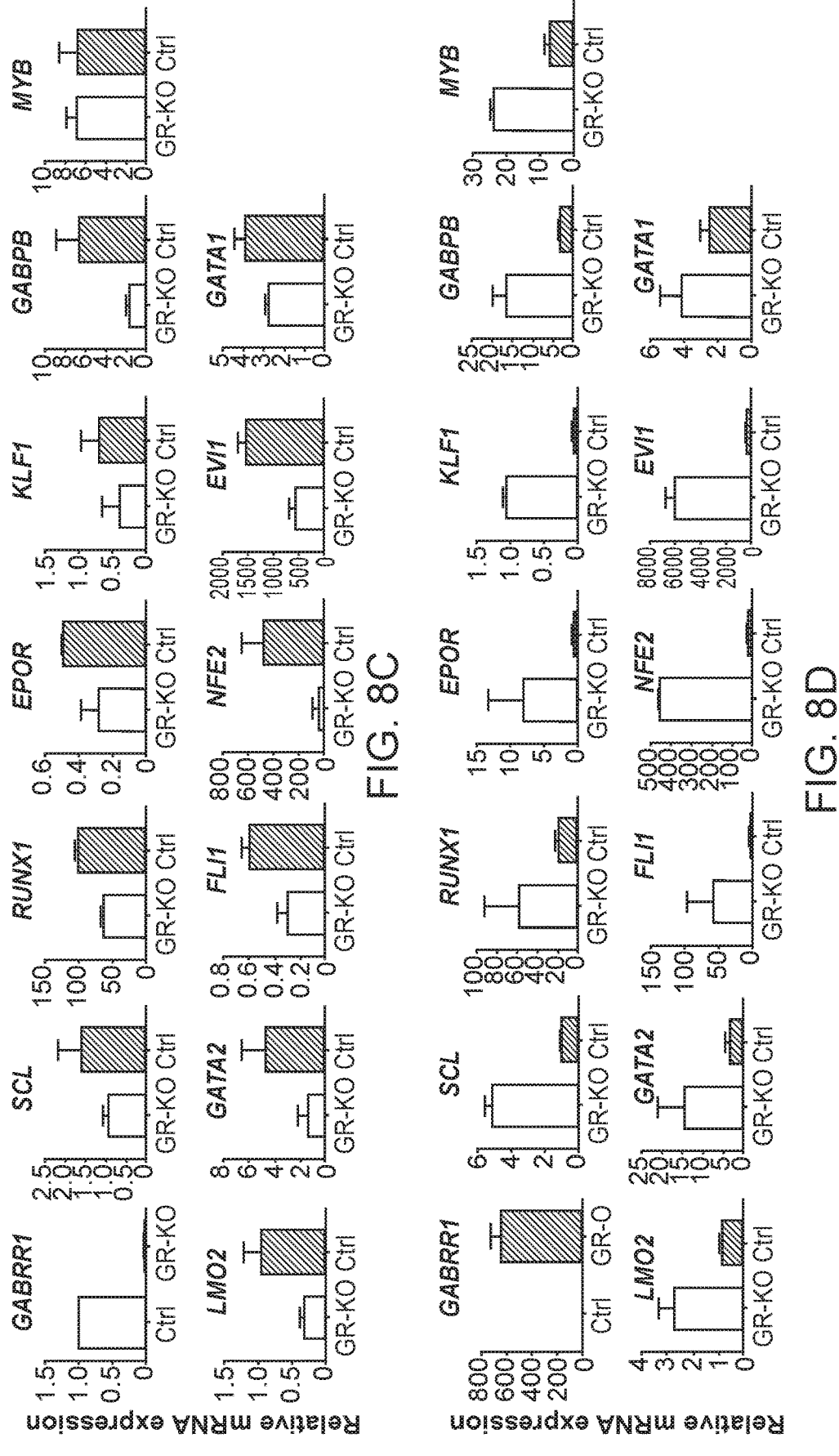
Figure 8E:
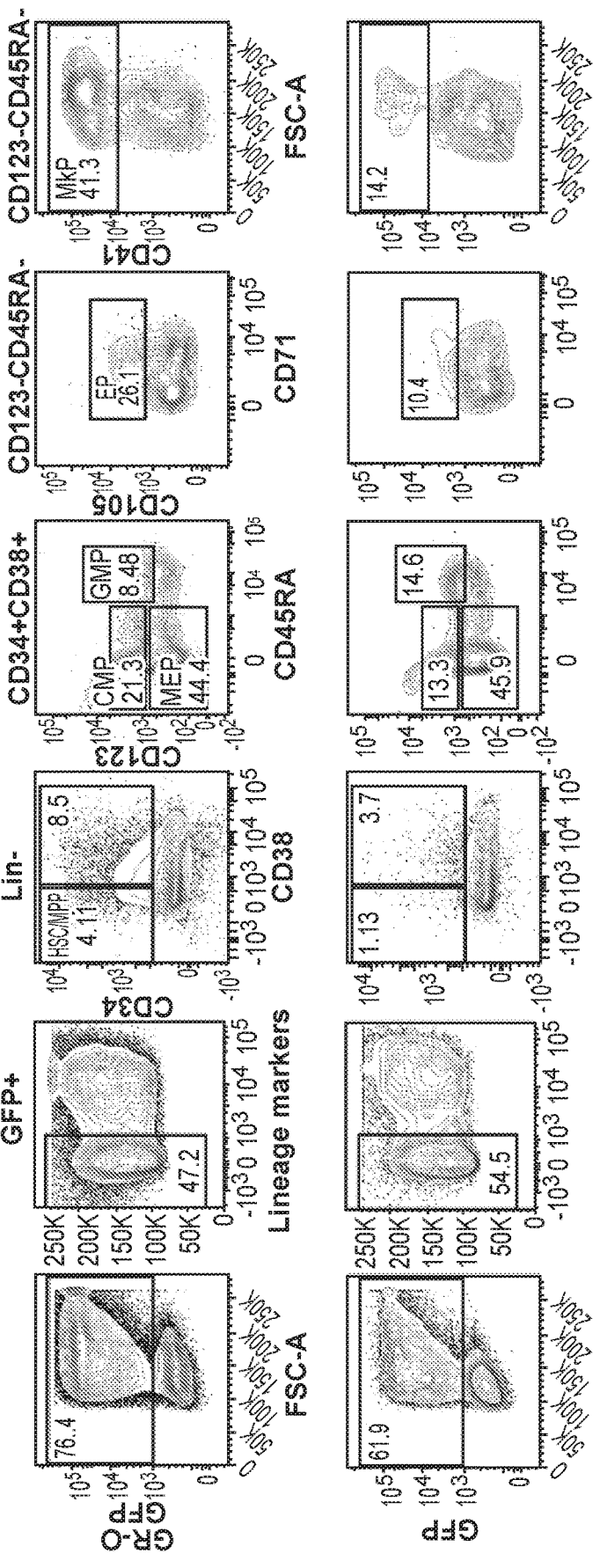

(MkP) and CD34+CD71+ (EP) percentage in 7-day differentiated CD34+ cells with GABRR1 knockout or overexpression with the non-treated or GFP-transduced cells as the control, respectively. FIG. 8C-8D. Gene expression analysis of GABRR1, megakaryocytic and/or erythroid cells-associated genes by real time PCR from bone marrow CD34+ after knockout FIG. 8C or overexpression FIG. 8D of GABRR1 and then 7 days of differentiation. Data shown are mean±SD from three replicates of the same group and are representative of at least three independent experiments. FIG. 8E Multicolor flow cytometry of human HSPCs after 7 days of differentiation of bone marrow CD34+ cells with GABRR1 overexpression. Data are representative of at least three independent experiments. GR-O, GABRR1 overexpression; GR-KO, GABRR1 knockout.

DETAILED DESCRIPTION OF THE EMBODIMENTS

In order for the present disclosure to be more readily understood, certain terms and phrases are defined below as well as throughout the specification. The definitions provided herein are non-limiting and should be read in view of what one of skill in the art would know at the time of invention.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments the mammal is human.

As used herein, a "therapeutically effective amount" refers to that amount of the therapeutic agent, e.g. a GABRR1 agonist, sufficient to prevent, treat or manage a disease or disorder. A therapeutically effective amount may refer to the amount of therapeutic agent sufficient to delay or minimize the onset of disease, e.g., delay or minimize thrombocytopenia that results from radiation, chemotherapy, and the like. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Megakaryocytic cells. Megakaryocytes (MKs) generate blood platelets which are active in clot formation at the site of injury. MKs are polyploid cells derived from hematopoietic stem cells and progenitor cells residing in the bone marrow. By extension of cytoplasmic protrusions through bone marrow sinusoids, MK release daily ~$1 \times 10^{11}$ platelets into the blood stream to sustain the count of circulating platelets. A decrease in platelet number, or thrombocytopenia, may occur following bone marrow failure (inherited or acquired, such as post-cancer treatment) or severe peripheral bleeding after trauma or surgery, and potentially leads to life-threatening hemorrhages.

Currently, prophylactic and therapeutic treatment essentially relies on transfusion of platelet concentrates, however, the increase in high-dose cancer therapy, advanced surgical procedures and the ageing population has led to a rising demand for platelets. In addition, platelet transfusion refractoriness in HLA class I alloimmunized chronically transfused patients and multiparous women necessitates the special provision of matched platelet units sourced from a small pool of genotyped recallable donors.

The differentiation of hematopoietic cells can be traced down specific lineages back to hematopoietic stem cells, which are characterized by self-renewal capacity and multipotent differentiation potential. This rare subpopulation of blood cells provides peripheral blood cells throughout an individual's lifetime. The bifurcation of myeloid/lymphoid lineages is believed to occur within multipotent progenitors (MPPs) during differentiation, where the myeloid lineage progenitors further lose differentiation potential into granulocyte/macrophage and erythroid linages and eventually produce common myeloid progenitors (CMP), MEPs and unipotent MkPs. However, the methods described herein are not limited by the theory of specific lineages, and may be applied to any pathway by which HSC differentiate to MK cells.

Factors that enhance production of megakaryocytes and platelets according to the methods described herein may act to skew HSC and progenitors derived therefrom to differentiation toward myeloid and megakaryocytic lineages; and/or may act to increase proliferation of MkP cells and production of platelets. As used herein, the term hematopoietic stem and progenitor cells may include, without limitation, hematopoietic stem cells, multipotent progenitor cells, common myeloid progenitor cells, megakaryocyte-erythroid progenitor cells, megakaryocyte progenitor cells, etc. See for example Chao et al, Cold Spring Harb Symp Quant Biol 2008. 73: 439-449, herein specifically incorporated by reference.

GABAA-ρ receptors (also known as GABA-ρ, GABAC, GABRR) receptors; are homopentameric ligand-gated ion channels (LGIC) composed of ρ subunits. They are members of the pentameric or Cys-loop LGIC superfamily comprising excitatory cation selective receptors such as nicotinic acetylcholine receptors; 5-HT3 receptors and zinc-activated channels; and inhibitory anion-selective receptors such as GABAA receptors, strychnine-sensitive glycine receptors and invertebrate glutamate-gated chloride channels. Receptors of this superfamily require five subunits to assemble a single ion channel. Exemplary human protein sequences may be found, for example in Genbank, NCBI Reference Sequence: NP_002033.2.

The Cys-loop receptors are analogous to each other in their structure, and they consist of three domains. The N-terminal extracellular domain is generally formed by 10 β-strands in two sheets that form a sandwich and two α-helices. This domain contains the orthosteric binding site and also the Cys-Cys disulfide bond forming the characteristic Cys-loop of 13 residues (also called β6-β7 loop). This loop is conserved across subunits belonging to this superfamily. This structure is believed to be important for both cell surface expression and cooperative interaction between the agonist binding sites and the channel gate. The second domain consists of the four transmembrane α-helices (TM1-TM4). TM2 forms the pore of the ion channel, whereas the remaining three TM helices form a hydrophobic environment to incorporate the pore into the plasma membrane. The third domain is an intracellular loop between TM3 and TM4 that is variable and of unknown structure. This loop has little residue conservation between different subunits or subunits of different subtypes.

Significant differences have been identified between various ionotropic GABA receptors based on physiological, pharmacological and biochemical properties. GABA is between 10- and 100-fold more potent at GABA-ρ receptors than heteromeric GABAA receptors, with slow activation and deactivation and less readily desensitized. GABAA receptors are well known to be modulated by agents such as benzodiazepines, barbiturates and neurosteroids, however GABA-ρ receptors are insensitive to these GABAA receptor modulators.

The term "modulating" as used herein means increasing or decreasing, e.g. activity, by a measurable amount. Compounds that modulate GABRR activity by increasing the activity of the receptors are called agonists. Compounds that modulate activity by decreasing the activity of the receptors are called antagonists. An agonist interacts with a GABRR to increase the ability of the receptor to transduce an intracellular signal in response to endogenous ligand binding. An antagonist interacts with a GABRR and competes with the endogenous ligand(s) or substrates) for binding sites) on the receptor to decrease the ability of the receptor to transduce an intracellular signal in response to endogenous ligand binding. Modulating compounds, i.e. agonists and antagonists, may be collectively referred to modulators.

The term "selective" as used herein means having the characteristic or property of being highly specific in binding, activity, or effect. Compounds described herein as selective for one GABA receptor over another may preferentially bind one isoform of GABBR1 v GABRR2, or one receptor over another, e.g. GABAA v GABRR. The degree of selectivity may vary, but preferably a selective compound would be at least tenfold selective for the desired target (e.g., GABRR1). More preferably, the compound would be 100- to 1000-fold selective. Alternatively, a compound may be selective the sense of producing a differential effect. For example, such a compound may bind two receptors with equal or similar affinity, but activate one while inhibiting the other.

For the purpose of this invention, the term "agonist" should be understood as including both full agonists as well as partial agonists, whereby a "partial agonist" should be understood as a compound capable of partially, but not fully, activating the GABRR1 receptor. In some embodiments an agonist is selective for GABRR relative to GABAA and GABAB receptors. In some embodiments an agonist is selective for GABRR1 relative to GABRR2 or GABRR3.

Examples of compounds having agonistic or partially agonistic affinity to GABRR receptors and which thus can be used according to the invention include without limitation: 4-aminobutanoic acid (GABA), trans-4-aminocrotonic acid (TACA), muscimol; cis-4-amino-crotonic acid (CACA), (+)-cis-2-(aminomethyl)cyclopropane carboxylic acid (CAMP); (±)-trans-2-(aminomethyl) cyclopropane carboxylic acid (TAMP); trans-2-methyl-4-aminocrotonic acid (2-MeTACA); 3-(aminomethyl)-1-oxo-1-hydroxy-phospholane (3-AMOHP); 3-(amino)-1-oxo-1-hydroxy-phospholane (3-AOHP); 3-(guanidine)-1-oxo-1-hydroxy-phospholane (3-GOHP); 4-aminocyclopent-1-enecarboxamide (4-AC-PAM); 4-amino-N-hydroxycyclopent-1-enecarboxamide (4-ACPHA), and the like.

The use of pharmaceutically acceptable salts of GABA agonists for the disclosed purposes is also included in the invention. They also can form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric or phosphoric acid or organic acids such as organic sulfonic acids and organic carboxylic acids. Salts of agonists with bases are, for example, alkali metal salts, e.g., sodium or potassium salts, or alkaline earth metal salts, e.g. calcium or magnesium salts as well as ammonium salts, such as those with ammonia or organic amines.

The use of optical isomers of agonists for the disclosed purposes is also included in the invention. Many known agonists such as for example baclofen and (3-amino-2-(S)-hydroxypropyl)methylphosphinic acid are chiral compounds due to the presence of an asymmetric carbon atom. Depending on the presence of asymmetric atoms, the agonists may be in the form of mixtures of isomers, particularly racemates, or in the form of pure isomers, especially enantiomers.

For use as a regulator/stimulator of megakaryopoiesis and treatment of thrombocytopenia the GABA receptor agonist may be used at doses appropriate for other conditions for which GABA receptor agonists are known to be useful. The typical daily dose of the active substance varies within a wide range and will depend on various factors such as for example the individual requirement of each patient and the route of administration. In general, dosages will be in the range of 1 µg to 100 mg per day and kg body weight, preferably 10 µg to 10 mg per day and kg body weight, more preferably 100 µg to 50 mg per day and kg body weight.

For clinical use, the compounds of the invention are formulated into pharmaceutical formulations for oral, rectal, parenteral, transdermal, or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention. vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

Therapeutic and Preventive Uses

In some embodiments, methods are provided for the treatment or prevention of thrombocytopenia, the method comprising administering to an individual suffering from, or at risk of developing thrombocytopenia. An effective dose or regimen of doses of a GABRR1 agonist is provided to the individual to increase production of megakaryocytes and platelets, and thereby alleviate thrombocytopenia.

The prevention or treatment against thrombocytopenia can be aimed at an increased level of active platelets. This means that platelet number becomes higher after administration of the agonist than prior to the administration. An amount effective to increase platelet counts in the subject is an amount, which causes an increase in the amount of circulating platelet levels. The actual levels of platelets achieved will vary depending on many variables such as the initial status of the immune system in the subject, i.e., whether the subject has mild to severe thrombocytopenia (e.g., resulting from an autoimmune disease or splenic sequestration).

In general, the platelet levels of a subject who has severe thrombocytopenia will initially be very low. Any increase in the platelet levels of such a subject, even an increase to a level that is still below a normal level, can be advantageous to the subject, since at the same time platelet function will be upregulated. The administration of the inhibitor aims to increase the number of platelets by at least 20, 50, 75 or 100%. Depending on the initial status of the individual (severe or low thrombocytopenia or normal platelet number), the individual will, after the administration of the inhibitor, display a low thrombocytopenia, a normal platelet number or a platelet number of normal levels). Alternatively, and more particularly in case of prevention of thrombocytopenia e.g. in combination with or before chemotherapy, administration of a GAGRR1 agonist can be aimed at a maintenance of the number of active platelets (i.e. preventing a significant decrease in the number of platelets expected as a result of chemotherapy). The methods may, for example, increase platelet counts to at least $20-50 \times 10^3/\mu l$, at least $50-100 \times 10^3/\mu l$, at least $100-150 \times 10^3/\mu l$, and up to a substantially normal level. Measurements may be monitored following treatment to determine efficacy.

As used herein, "thrombocytopenia" is any disorder in which the platelet level in the affected individual fall below a normal range of platelet numbers for that individual, due to disturbance in production distribution or destruction. In humans, normal blood platelet levels range from about 150,000 to 300,000 per microliter peripheral blood. With a platelet level of 100,000 per microliter patients have no abnormal bleeding even with major surgery; with a platelet count of 50,000 to 100,000 per microliter, patients may bleed longer than normal with severe trauma; with a platelet count of 20,000 to 50,000 per microliter, bleeding occurs with minor trauma but spontaneous bleeding is unusual; with a platelet count of less than 20,000, patients may have spontaneous bleeding and when the platelet count is less than 10,000 per microliter, patients are at high risk for severe bleeding.

Thrombocytopenia also refers to a decrease in platelet number in an individual when compared to the platelet number measured at a certain reference point in that individual. The decrease in platelet number in the individual can be a decrease in more than 20%, 30%, 40%, 60%, 80%, 90%, 95% or even more, compared to value at the reference point. A decrease in platelet number when compared to the platelet number measured at a certain reference point, can in certain individuals be accompanied with changes in bleeding, while in other individuals a comparable decrease will not be accompanied with changes in bleeding. The reference point mentioned, can be for instance the start of a therapy such as a radiation or chemotherapy.

Thrombocytopenia includes infection-induced thrombocytopenia, treatment-induced thrombocytopenia and others. Treatment-induced thrombocytopenia is caused by therapeutic treatments such as gamma irradiation, therapeutic exposure to radiation, cytotoxic drugs, chemicals containing benzene or anthracene and other drugs such as chloramphenicol, thiouracil, and barbiturate hypnotics. Other types of thrombocytopenia" comprise disorders characterised by a low level of platelets in peripheral blood, which are caused by any mechanism other than infectious agents or therapeutic treatments causing thrombocytopenia. Factors causing this type of thrombocytopenia include, but are not limited to, rare bone marrow disorders such as congenital amegakaryocytic hypoplasia and thrombocytopenia with absent radii (TAR syndrome), an increase in spleen size, or splenomegaly, caused by portal hypertension, secondary to liver disease, or macrophage storage disorders such as Gauchers disease, autoimmune disorders such as idiopathic or immune thrombocytopenic purpura (ITP), vasculitis, hemolytic uremic syndrome, thrombotic thrombocytopenic purpura (TTP), disseminated intravascular coagulation (DIC) and prosthetic cardiac valves. ITP is by far the most frequent type in this group of thrombocytopenias.

A "subject having thrombocytopenia" is a subject having any type of thrombocytopenia and includes but is not limited to non-chemotherapeutic-induced thrombocytopenia, or chemotherapeutic-induced thrombocytopenia. "A subject at risk of developing thrombocytopenia" is a subject who has a high probability of acquiring or developing thrombocytopenia. For example, a patient with a malignant tumor who is prescribed a chemotherapeutic treatment is at risk of developing treatment-induced thrombocytopenia and a subject who has an increased risk of exposure to infectious agents is at risk of developing infection-induced thrombocytopenia.

The compositions for inducing platelet production, comprising an effective quantity of a GABRR1 agonist can be in admixture with pharmaceutically acceptable diluents, carriers or excipients. This property of stimulating platelet production of the molecule makes it a useful adjunct in the therapy of patients suffering from acute thrombocytopenia, for example, as a result of chemo- or radiotherapy of various cancers.

The term medicament relates to a composition comprising molecules as described above and a pharmaceutically acceptable carrier or excipient (both terms can be used interchangeably) to treat diseases as indicated above. The 'medicament' may be administered by any suitable method within the knowledge of the skilled person. The preferred route of administration is parenterally. For parenteral administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the compound is given at a dose between 0.1 μg/kg and 10 mg/kg, as a bolus dose or by continuous infusion, including continuous subcutaneous delivery via an osmotic minipump.

In Vitro Applications

The methods described herein for enhancing megakaryocyte production also find use in enhancing the production of megakaryocytes and MkP cells from stem cells, e.g. HSC, iPSC, etc. and/or hematopoietic progenitor cells, e.g. MPP, CMP, MEP, etc. when cultured in vitro culture.

The cell population may be grown in vitro under various culture conditions. Culture medium may be liquid or semisolid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Of particular interest for the subject cells are factors that promote thrombopoiesis, including thrombopoietin. Specific growth factors that may be used in culturing the subject cells include steel factor (c-kit ligand), Flk-2 ligand, IL-11, IL-3, GM-CSF, erythropoietin and thrombopoietin. The specific culture conditions are chosen to achieve a particular purpose, i.e. differentiation into megakaryocytes, maintenance of progenitor cell activity, etc. In addition to the factors themselves, the activity of the factor may be provided through mimetics, antibodies that bind the cognate receptor, and the like. For example, a number of thrombopoietin mimetics are known in the art. Duffy et al. (2002) J Med Chem. 45(17):3576-8 identify a pharmacophore for thrombopoietic activity; and Cwirla et al. (1997) *Science* 276:1696 describe a mimetic of thrombopoietin that is highly active. In addition to, or instead of growth factors, the subject cells may be grown in a co-culture with stromal or fibroblast feeder layer cells. Stromal cells suitable for use in the growth of hematopoietic cells are known in the art.

The progenitor cells may be used in conjunction with the culture system in the isolation and evaluation of factors associated with the differentiation and maturation of megakaryocytes and platelets. Thus, the progenitor cells may be used in assays to determine the activity of media, such as conditioned media, evaluate fluids for growth factor activity, involvement with dedication of lineages, or the like.

Genes may be introduced into the cells, e.g. the HSC or IPSC for a variety of purposes, e.g. replace genes having a loss of function mutation, markers, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

The resulting MKP or megakaryocyte cells may be used in transplantation for reconstitution of platelet function in a recipient, e.g. in thrombocytopenia. The cells may be administered in any physiologically acceptable medium, normally intravascularly, although they may also be introduced into bone or other convenient site, where the cells may find an appropriate site for regeneration and differentiation. Usually, at least $1 \times 10^4$ cells/kg body weight will be administered, and may be $10^5$, $10^6$, $10^7$ or more/kg body weight. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FOS, 40% RPMI 1640 medium. Once thawed, the cells may be expanded by use of growth factors and/or stromal cells associated with progenitor cell proliferation and differentiation.

The invention now being fully described, it will be apparent to one of ordinary skill in the art that various changes and modifications can be made without departing from the spirit or scope of the invention.

EXAMPLES

The GABA Receptor GABRR1 is Expressed on and Functional in Hematopoietic Stem Cells and Megakaryocyte Progenitors GABRR1 is a rho subunit receptor of GABA, the major inhibitory neurotransmitter in mammalian brain. Most of the investigations of its function have been focused on the nervous system, and its regulatory role in hematopoiesis has not previously been reported. In this study, we found GABRR1 is mainly expressed on subsets of human and mouse hematopoietic stem cells (HSCs) and megakaryocyte progenitors (MkPs). GABRR1-negative (GR−) HSCs led to higher donor derived hematopoietic chimerism than GABRR1-positive (GR+) HSCs. GR+ but not GR− HSCs/MkPs respond to GABA in patch clamp studies. Inhibition of GABRR1 via genetic knockout or antagonists inhibited MkP differentiation and reduction of platelet numbers in blood, Overexpression of GABRR1 or treatment with agonists significantly promoted MkP generation and megakaryocyte colonies. Thus, this study identifies a link between the neural and hematopoietic systems and provides methods for manipulating GABA signaling for platelet-required clinical applications.

Gene expression commons designed by us to perform probeset meta-analysis for a particular microarray platform and profile absolute expression of any gene on the microarray, has established both human and mouse hematopoiesis models. In this study, we first determined the expression of all GABA receptors ($\alpha$1-6, $\beta$1-3, $\gamma$1-3, $\delta$, $\epsilon$, $\theta$, $\pi$, $\rho$1-3) in GEXC "mouse hematopoiesis" and found that MkP cell populations were selectively GABRR1$^+$, and other GABA receptors were not expressed in any of the HSPC populations (FIG. 1A and FIG. 5A). RT-PCR of hematopoietic cell populations confirmed its expression pattern (FIG. 1B). The GABAA-$\rho$ receptors (GABRR1-3) are ligand-gated ion channels that play physiological roles in retina, spinal cord and brain. GABRR1 can be composed entirely of homo- or hetero-pentamer $\rho$ subunits. Because only GABRR1 is expressed, we expect that our hematopoietic cells only could form homooligomers.

Further analysis of mouse bone marrow by flow cytometry revealed that, GABRR1 is mainly expressed on a subset of HSCs (8.18%±1.53%) and MkPs (3.04%±0.7%) (FIG. 1C and FIG. 5B). Other blood lineage (CD45$^+$) cells were negative (FIG. 5C). GABRR1 expression in immuno-phenotypically defined HSCs (pHSCs, CD34−Flk2−CD150+ KLS), MPPa (CD34+Flk2−CD150+KLS) and MPPb (CD34+Flk2−CD150−KLS), showed 1%-3% of those early stem and progenitors cells expressed GABRR1 (FIG. 5D). In addition, GABRR1 expression was detected in a higher level in platelet-biased HSCs (FIG. 5E).

Gabrr1$^+$ (GR$^+$) and Gabrr1$^-$ (GR$^-$) HSCs or MkPs cells were then purified and tested by electrophysiological recording using patch-clamp techniques. The clamped cell was held at various membrane potentials and incubated with 1 mM GABA (FIG. 1D), In GR+ MkP cells, we observed a prominent GABA-induced inward current, but not in GR− cells (FIG. 1E-F). Similarly, significant currents were induced by GABA application to GR+ HSCs, although the amplitude appears to be smaller than that in GR+ MkP cells (FIG. 1G-H), Taken together, these results show that GABRR1 expressed in HSCs and MkPs is functional as an ion channel.

We then sought to identify the source of GABA in bone marrow, None of HSPCs we isolated released detectable levels of GABA. Since glutamic acid decarboxylase 1 (GAD1) and GAD2 synthesize GABA from glutamate, we searched for the bone marrow cell source of GABA by examining the expression of GADs by real time PCR. Among all cells tested, including bone marrow cell mixtures, HSPC populations, mature blood cells, skeletal lineage (Tie2− AlphaV+) cells, non-skeletal and non-endothelial (Tie2− AlphaV−) and all Tie2+ cells[21], only Tie2+ cells from bone marrow cell suspension fraction showed expression of GADs by real time PCR analysis (FIG. 5F). Tie2 marks rare HSCs, early progenitors of, and mature, endothelial cells, and perhaps other cells not yet placed in a lineage.

Because cell suspensions can exclude some sessile cells, we sectioned mouse bones and performed in situ immuno-fluorescence staining for GADs using antisera commonly used to detect potential GABA-ergic cells. GAD positive cells appear in highest concentration at the growth plate and the femoral epiphysis (FIG. 1I-J). More staining showed that GABA and vesicular GABA transporter (vGAT) could also be detected in the same region. However, co-staining of GADs with endothelial cell surface markers, including CD31 and VE-cadherin, shows that there are only very rare double positive cells (FIG. 5G), so the Tie2+ cells are not endothelial cells in general. The GAD+ cells in the epiphysis resemble cartilage progenitors. Synaptophysin can be detected with antisera to SP4 (FIG. 1I), and here we detect some positive cells also in the epiphysis, but these do not have the morphology of neurons. Those results suggested that non-neural cells in the bone and bone marrow are candidates for GABA production and release, but do not definitively show which cells are GABAergic.

We isolated GR+ and GR− HSCs and MkPs and examined the gene expression patterns by real time FOR. We checked the expression of HSC and MkP shared transcripts, HSC, MEP, MkP, myeloid, erythroid, lymphoid and platelets lineage associated genes and found that both GR+ and GR− HSC or MkP cells expressed corresponding cell lineage specific genes (FIG. 1K and FIG. 6A). GR− HSC and GR− MkP populations maintained higher expression levels of multipotency genes than GR+ populations, while GR+ populations exhibit higher myeloid, platelet and erythroid genes and none of them expressed lymphoid genes (FIG. 1K and FIG. 6A). After in vitro differentiation of GR+ and GR− HSCs, flow cytometry analysis showed that GR− cells contained more progenitor cells, which is consistent with gene expression analysis results (FIG. 6B).

We then characterized GABRR1-expressing and negative cells by HSC transplantation. GR+ and GR− HSCs from CD45.2 C57BL/6 mice were transplanted with supporting CD45.1 bone marrow cells into irradiated CD45.1 mouse recipients. The results, presented in FIG. 2A-B and FIG. 6C, showed GR− HSCs have higher full multilineage reconstitution than GR+ HSCs. Twenty weeks after transplantation GR− HSC transplanted mice have higher frequencies of HSCs, MPPs, MkPs, GMPs and EPs (FIG. 20). Secondary transplantation showed GR− HSCs have the capacity of robust multilineage chimerism, suggesting they are long term HSCs (FIG. 2D-E).

To further address how Gabrr1 is involved in the regulation of hematopoiesis, we used Gabrr1 knockout mice B6; 129S4-Gabrr1tm1Llu/J (GR$^{-/-}$ mice), and used B6129SF2/J hybrid mice as controls. GR$^{-/-}$ mice had significantly lower levels of blood platelets (87.7%±4.92%), while WBC, LYM, HGB and RBC in GR$^{-/-}$ mice were not significantly changed (FIG. 20). Among c-Kit enriched HSPCs. HSCs were decreased in GR$^{-/-}$ mice to 50% the level of these control mice, while MkPs present in the c-Kit enriched marrow cells were reduced by 13%±2.6% compared with controls (FIG. 2E and FIG. 7A).

We then examined the effects of agonists and antagonists of Gabrr1 in C57BL/6J mice, including the agonists GABA, TACA, Muscimol and antagonist SR95531. After 7 days of treatment, we found that GABA treatment increased platelet numbers by 17.7%±11.2%, and treatment by Muscimol and TACA showed increases of 35.0%±13% and 24.6%±19.0%, respectively (FIG. 2F). RBC numbers were slightly increased with these treatments. SR95531 did not affect platelet number significantly (FIG. 2F). Bone marrow MkPs were increased by several different agonist treatments, including GABA by 63.7%±24.4%, Muscimol by 55.0%±26.7% and TACA by 23.3%±31.1%. HSCs and MPPs were also significantly increased by 1.5-2.5 fold. Interestingly, EP and Pre CFU-E were also increased, consistent with the RBC increase in peripheral blood (FIG. 2G and FIG. 7B).

To investigate the role of GABRR1 in human hematopoiesis, we checked GABRR1 cell surface protein expression by FACS, GABRR1 is mainly expressed in human HSC/MPP (3.45%±1.0%), CMP (1.82%±0.34%), and MkP (1.60%±0.16%) (FIG. 3A). RT PCR analysis confirmed the result (FIG. 3B). HSC or MkP gene expression analyses by RT FOR in GR+ and GR− HSC/MPP or MkP cells showed similar patterns as in mouse HSPCs, with higher multipotent gene expression in GR− cells (FIG. 30). Next, we differentiated Lin-CD34+GR+ and Lin-CD34+GR− cells in vitro. The results showed Lin-CD34+GR− cells included more progenitor cells (FIG. 3D). Functional megakaryocyte colony forming assay showed GR− Lin-CD34+ cells generated more MK colonies than GR+ Lin-CD34+ cells (FIG. 3E), Those results indicate that both in mouse and human, GABRR1 influenced HSC multipotency and megakaryocyte differentiation.

We then genetically manipulated GABRR1 expression levels through lentivirus-mediated gene knockout and overexpression. Firstly, CRISPR/Cas9 mediated gene knockout was used to eliminate GABRR1 expression, PCR analysis confirmed its expression level was reduced in CD34+ cells (FIG. 80). Then, CD34$^+$ cells were cultured and differentiated by supplementing cytokines TPO, hSCF, hIL3, hIL6 and Flt3 in vitro (FIG. 8A). Both CD34$^+$CD41$^+$ (selective MkP/megakaryocyte markers) and CD34$^+$CD71$^+$ (selective EP/erythrocyte markers) cells were reduced by 30-40% (FIG. 3F and FIG. 8B).

Overexpression of GABRR1 in human CD34+ cells led to a significant increase of CD34+CD41+ and CD34+CD71+ populations by approximately 3-4 fold (FIG. 3F and FIG. 8B). Using RT PCR analysis, we analyzed gene expression levels of megakaryocyte related genes, erythroid genes and genes of both lineages in both GABRR1 knockout and overexpression cells. The results showed the RNA expression of those genes were significantly enhanced in GABRR1 overexpressing cells while reduced in GABRR1-knockout cells (FIG. 8C-D). Starting with 10,000 CD34+ cells, we obtained 52 megakaryocytic colonies from GABRR1-overexpressing cells, 8 from GABRR1-knockout cells, 30 colonies from non-virus treated control and 20 from the vector control transduced groups (FIG. 3G).

Since HSC differentiation into MkPs involves several steps, we next determined at which stage GABRR1 functions. By analyzing the frequencies of HSPCs populations in GABRR1 overexpressing cells (FIG. 3H and FIG. 8E), we found that HSC/MPP increased to 263.6%±51.6% and almost all downstream progenies also were increased (CMP to 267.3%±53.6%, MEP to 263.3%±68.7%, MkPs to 254.5%±92.6%, EPs to 423.2%±67. Those results indicated GABRR1 affects MkP generation at the early stage of differentiation.

We treated human CD34+ cells with different agonists and antagonists of GABRR1. The CD34+CD41+ and CD34+ CD71+ populations increased approximately 2-4 fold, respectively with the treatment of GABRR1 agonists (GABA, TACA, and Muscimol) and decreased dramatically when treated with GABRR1 antagonist SR95531 (FIG. 4A-B). GABA was the most effective treatment that increases MkPs to 168.9%±41.0%. The other agonists also produce 1.5-2 fold increases in the MkP frequency. The antagonist SR95531 decreased the frequency of all HSPCs tested, especially the MkPs to 40.3%±13.6% (FIG. 4C-D). Real-time PCR analysis demonstrated that GABA significantly increased the megakaryocyte-related genes (FIG. 4E) while the other agonists showed similar effects. CFU-MK assay showed that GABA, Muscimol and TACA generated a 1-3 fold increase in megakaryocyte colonies while SR 95531 decreases this by 40%, (FIG. 4F). These results indicated that GABRR1-mediated GABA signaling could regulate human hematopoiesis.

To date, the precise control of HSC differentiation to MkPs is largely unknown, and there is currently no efficient way to produce MkPs from HSCs for clinical applications. In our study, we have identified a potential regulator of MkPs both in mouse and human. We found that GABRR1 is expressed in subsets of HSCs and MkPs. Inhibition of GABRR1 signaling by genetic knockout or antagonists significantly decreased megakaryocyte and platelet differentiation, while overexpression of GABRR1 or agonist treatment increased megakaryocytic lineage development.

Regulation of hematopoiesis by the nervous system has been reported and is an active area of research, Here in our study, we identified a new and conserved link between the neural product GABA and hematopoietic systems in mice and human and provide a new strategy for producing MkPs and then platelets by manipulating GABRR1-mediated GABA signaling.

References Erdo, S. L. & Wolff, J. R. gamma-Aminobutyric acid outside the mammalian brain. J Neurochem 54, 363-372 (1990). Seita, J. & Weissman, I. L. Hematopoietic stem cell: self-renewal versus differentiation. Wiley Interdiscip Rev Syst Biol Med 2, 640-653, (2010). Nakorn, T. N., Miyamoto, T. & Weissman, I. L. Characterization of mouse clonogenic megakaryocyte progenitors. Proc Natl Acad Sci USA 100, 205-210 (2003). Klimchenko, O. et al. A common bipotent progenitor generates the erythroid and megakaryocyte lineages in embryonic stem cell-derived primitive hematopoiesis. Blood 114, 1506-1517, (2009). Seita, J. et al. Gene Expression Commons: an open platform for absolute gene expression profiling. PLoS One 7, e40321, (2012), Olsen, R. VV. & Sieghart, W. International Union of Pharmacology. LXX. Subtypes of gamma-aminobutyric acid (A) receptors: classification on the basis of subunit composition, pharmacology, and function. Update. Pharmacol Rev 60, 243-260, (2008). Sim, X., Poncz, M., Gadue, P. & French, D. L. Understanding platelet generation from megakaryocytes: implications for in vitro-derived platelets, Blood 127, 1227-1233, (2016). Moreau, T, et al, Large-scale production of megakaryocytes from human pluripotent stem cells by chemically defined forward programming. Nat Commun 7, 11208 (2016). Boitano, A. E., de Lichtervelde, L., Snead, J. L., Cooke, M. P. & Schultz, P. G. An image-based screen identifies a small molecule regulator of megakaryopoiesis. Proc Natl Aced Sci USA 109, 14019-14023, (2012). Berridge, M. V., Ralph, S. J. & Tan, A. S. Cell-lineage antigens of the stem cell-megakaryocyte-platelet lineage are associated with the platelet IIb-IIIa glycoprotein complex. Blood 66, 76-85 (1985). Mori, Y., Chen, J. Y., Pluvinage, J. V., Seita, J. & Weissman, I. L. Prospective isolation of human erythroid lineage-committed progenitors, Proc Natl Acad Sci USA 112, 9638-9643, (2015).

Materials and Methods

Mice. C57BL/6J, B6.SJL-Ptprca Pepcb/BoyJ, B6; 129S4-Gabrr1tm1Llu/J and B6129SF2/J mice were purchased from The Jackson Laboratory, and were bred at our animal facility according to NIH guidelines. Male mice of similar ages (6-10 weeks) were used in the experiments. All animal protocols were approved by the Stanford University Administrative Panel on Laboratory Animal Care.

Plasmids. The LentiCRISPR V2 plasmid was purchase from Addgene. The sgRNA of GABRR1 was designed and cloned into the all-in-one CRISPR lentiviral vector. The pCDH-MSCV-MCS-EF1-GFP+Puro cDNA cloning and expression vector (CD713B-1) was purchased from SBI. GABRR1 cDNA (NM_001256703.1) was cloned from pDONR223, which was purchased from DNASU and inserted under the MSCV promoter. The same empty vector without GABRR1 cDNA was used as the vehicle control.

Cell Isolation and Culture. Human bone marrow mononuclear cells were purchased from AllCells and cultured in StemSpan™ Serum-Free Expansion Medium II (SFEM II, StemCell Technologies), supplemented with 20 ng/ml hSCF (PeproTech), hTPO, hIL-3, hIL-6 and Flt3 (R&D Systems). Mouse bone marrow mononuclear cells were isolated from mice and cultured in StemSpan™ SFEMI (StemCell Technologies), supplemented with mTPO and mSCF (PeproTech). GABA, Muscimol, TACA or SR 95531 hydrobromide (Tocris) are added in the presence of all the cytokines. Medium was changed every other day.

Mouse injection. Mice were randomly grouped and injected once everyday using GABA agonists and antagonists. Muscimol 2 mg/kg, TACA 2 mg/kg and SR95531 4 mg/kg was injected by i.p. The mice were treated for 7 days and then complete blood cell counting was done with the HemaTrue Hematology Analyzer (HESKE).

Transplantations and peripheral blood analyses. B6.SJL-Ptprca Pepcb/BoyJ (Jackson Laboratory) recipient mice were lethally irradiated at a single dose of 9.1 Gy. GR+ and GR– HSCs were sorted out from C57BL/6J mice by flow cytometry and transplanted into recipient mice, together with $2 \times 10^5$ supporting cells from the same strain of recipient mice, by retro-orbital venous plexus injection. Peripheral blood was analyzed at 4, 8, 12 and 16 weeks after transplantations. Each time blood was collected from the tail vein and were subsequently lysed using BD Pharm Lyse Buffer (BD Pharmingen), as per the manufacturer's protocol, for 3 min on ice. Leukocytes were stained with antibodies against CD45.1, CD45.2, CD11b, Gr-1, B220, CD3, and NK-1.1.

Virus Production and Transduction. 293T cells are cultured in DMEM supplanted with 10% FBS, Virus was prepared through transfection in 293T by calcium phosphate method with package vectors pVsVg and psPAX2 and backbone vector. Virus was harvested 48 hours later and dead cells were removed with 0.45 um filter. Virus supernant was concentrated and Retronectin (Clonetech) was used to pre-coat nontreated plates following manufacturer's instruction. After BSA blocking and PBS washing, virus was coated into the plate by spinning at 2000 g for 2 hours. Cells were reseeded in those well for virus transduction, Three days later, 2 ug/ml puromycin was added in fresh medium for 7 days.

Colony-Forming Unit Assay. Colony forming assay was performed using the MegaCult™-C Complete Kit with Cytokines (Stemcell Tech, 04971)) following manufacturer's instruction, Colonies were counted after 12-14 days of culture and megakaryopoietic colonies were stained using antibody provided in the kit.

Flow Cytometry. Mouse bone marrow cells were harvested, washed, and resuspended in PBS containing 2% FBS, and subjected to the staining process with antibodies at their optimal concentrations. Cells were firstly blocked with Rat IgG. Then, to enrich HSCs and progenitor populations, cells were stained with APC-conjugated anti-c-Kit (2B8) and then with anti-APC magnetic beads (Miltenyi Biotec) after washing. The c-Kit+cells were eluted from LS columns (Miltenyi Biotec). Those cells then stained with the antibody cocktail directed against cell surface antigens as follows: for early progenitor analysis, Sca-1, Flk2, CD150, CD34, IL-7R, CD16/32, c-kit and the lineage markers Ter-119, B220, CD3, CD4, CD8a, Gr-1, CD11b, CD41. For late stage populations, cells were stained with antibodies specific for Sca-1, Endoglin [CD105], CD150, CD16/32, c-kit [CD117] and the lineage markers for 30 min at 4° C., DNA dye was used for the live/dead cells staining.

Surface marker cocktail of mouse hematopoietic stem and progenitor populations:

HSC: Lin-c-kit+Sca1+CD150+Endoglin+

MPP: Lin-c-kit+Sca1+Endoglin–CD150–

GMP: Lin-c-kit+Sca1– CD41–FcgRII+

EP: Lin-c-kit+Sca1– CD41–FcgRII–Endogilin+CD150–

MkP: Lin-c-kit+Sca1– CD150+CD41+

PreGM: Lin-c-kit+Sca1– CD41–FcgRII–Endogilin–CD150–

Pre CFU-E: Lin-c-kit+Sca1– CD41–FcgRII–Endogilin+ CD150+

MEP: Lin-c-kit+Sca1– CD41–FcgRII–Endogilin–CD150+.

Human bone marrow or cord blood cells were stained in a similar way using Rat IgG for blocking and PI for viability. Human cells were stained with the antibodies cocktails as follows: CD34, CD38, CD45RA, CD123, CD71, CD105, CD41 and the lineage markers CD2, CD4, CD8, CD11b/ Mac-1, CD14, CD19, CD20, CD56 and CD235a. The GABRR1 antibodies were also used for staining (Bloss Antibodies).

Surface marker cocktail of human hematopoietic stem and progenitor populations:

HSCs/MPPs: Lin-CD34+CD38–

MkP: Lin-CD34+CD38+CD123–CD45RA–CD41+

CMP: Lin-CD34+CD38+CD123lowCD45RA–

MEP: Lin-CD34+CD38+CD123–CD45RA–

GMP: Lin-CD34+CD38+CD123+CD45RA+

EP: Lin-CD34+CD38+CD123–CD45RA–CD71+ CD150+.

Before analysis and sorting, cells were passed through 70 μm strainers. Flow cytometry and cell sorting were performed on a FACS Aria II cell sorter (BD Biosciences) and analyzed using FlowJo software (BD Biosciences).

RNA isolation and Real-Time PCR. Total RNA was extracted by RNeasy Plus Micro kit and RNeasy MinElute Cleanup Kit following manufacturer's instructions (Qiagen). Synthesis of cDNA was performed with the Super-Script™ III Reverse Transcriptase (ThermoFisher Scientific). Real time PCR was done using the Fast SYBR® Green Master Mix (ThermoFisher Scientific) on the 7900 Fast Real-Time PCR System (Applied Biosystems). PCR products were analyzed on a 2% agarose gel.

Electrophysiology. Whole-cell voltage-clamped recordings were made from the dissociated blood cells perfused in oxygenated ACSF containing the following (in mM): 119 NaCl, 26 NaHCO3, 10 glucose, 1.25 NaH2PO4, 2.5 KCl, 2 CaCl2, 1 MgCl2, 2 Na-pyruvate, and 0.5 ascorbic acid, pH 7.4. The cells were visualized under infrared differential interference contrast (IR-DIC) video microscopy (Axioskop 2; Zeiss) and had a diameter of 5-10 Patch pipettes (resistance of 5-7 MΩ) were pulled using borosilicate glass (WPI) on a two-stage vertical puller (Narishige). Cells were voltage clamped at various levels between –80 mV to 60 mV. The pipette internal solution contains (in mM): 120 Cs—Cl, 20 tetraethylammonium-Cl, 20 HEPES, 2 EGTA, 4 MgATP, 0.4 NaGTP, 10 phosphocreatine.

Currents were evoked by puffing locally GABA of a saturating concentration at 1 mM to activate all functional GABAARs on the cell. The drug was applied through a second pipette (resistance of 3-4 MΩ) connected to Picos-pritzer (Cleveland, OH, USA) at a pulse duration of 100 ms and pressure of 5-10 kPa.

Gene Expression Commons. Gene expression common has large-scale publicly available microarray data and perform probeset meta-analysis for a particular microarray platform. GABRR1 expression analysis in mouse hematopoietic stem and progenitor cells in gene expression commons revealed that of 39 hematopoietic stem, progenitor and mature populations in adult mouse bone marrow, spleen, and thymus, it is uniquely expressed in megakaryocytic progenitors (MkPs), which indicates that GABRR1 can play a role in megakaryopoiesis.

Immunohistochemistry. Skeletally mature, 8-week old, male, C57BL/6J mice (Jax 000664) were euthanized as per our Stanford approved APLAC protocol. The femurs were isolated immediately and fixed in 4% paraformaldehyde overnight at 4 C. The femurs were then washed twice in PBS and decalcified in 4M EDTA at 4 C for 2 weeks with EDTA change every alternate day. Following de-calcification, the femurs were then transferred into a 30% sucrose solution for 24 hours at 4 C. The tissue was then embedded in OCT compound (Scigen, 4583) and stored at –20 C until cryo-sectioning, Burn sections were taken. The sections were stored at –20 C until IHC was performed. Slides for IHC were washed twice with 0.25% Triton X-100 diluted in TBS at room temperature for 5 minutes each. The slides were then blocked with 5% anti-donkey and 5% anti-goat antibodies to reduce non-specific binding of the secondary antibodies for 2 hours at room temperature. Primary antibodies (Rabbit anti-mouse GAD 65-67, Abcam GR168030 and rat anti-mouse CD31, BD Pharmingen 558736) diluted 1:250 in TBS with 1% BSA were then added to the sections and allowed to incubate at 4 C overnight. After incubation, the slides were then washed twice with 0.25% Triton X-100 diluted in TBS at room temperature for 2 minutes each. The secondary antibodies (Donkey anti-rabbit AF594, Life technologies, 1256153 and goat anti-rat AF488, Invitrogen, 1156624) were then added diluted 1:500 with TBS with 1% BSA at room temperature for 1 hour. During this time, the sections were kept in the dark to prevent photo-bleaching. The slides were then rinsed twice with TBS at room temperature for 5 minutes each. Following the secondary stain, the slides were stained with DAPI (DAPI, Biolegend, B222486) diluted 1:1000 in TBS at room temperature for 10 minutes. The slides were then rinsed twice with TBS at room temperature for 5 minutes each. Aqueous mounting media (Fluoromount G, eBioscience, E099088) was used to mount the tissues. Slides were imaged using an SP8 inverted confocal microscope. Image J software (FIJI™) was used to reconstruct the confocal images.

Statistics. All the experiments were repeated at least 3 times. No blinding was done for any of these experiments. Two tailed Student's t-test was used for paired comparison and one way ANOVA for multiple comparisons. p value less than 0.05 was considered significant.

What is claimed is:

1. A method for increasing production of megakaryocytic lineage cells from CD34+ hematopoietic stem or progenitor cells in vitro, the method comprising: contacting the CD34+ hematopoietic stem or progenitor cells in culture with an effective dose of a γ-aminobutyric acid rho receptor (GABRR) agonist, wherein the GABRR receptor is GABRR1, wherein the CD34+ hematopoietic stem or progenitor cells are one or more of hematopoietic stem cells (HSC), multipotent progenitors (MPP), common myeloid progenitors (CMP) and megakaryocyte erythroid progenitors (MEP);

measuring for the presence of megakaryocytic lineage cells selected from megakaryocyte progenitor cells (MkP), megakaryocytes and platelets in the culture;

wherein production of megakaryocytic lineage cells in the culture is increased relative to culture in the absence of the GABRR1 agonist.

2. The method of claim 1, wherein the agonist is a selective agonist for GABRR1.

3. A method of increasing platelet levels in a mammalian subject, the method comprising:

administering in vivo to the mammalian subject a γ-aminobutyric acid rho receptor 1 (GABRR1) agonist in a dose effective to increase platelet levels in the subject; and measuring an increase in megakaryocytic lineage cells selected from megakaryocyte progenitor cells, megakaryocytes and platelets, wherein platelet levels are increased relative to an untreated control.

4. The method of claim 3, wherein the subject is human.

5. The method of claim 4, wherein the subject suffers from thrombocytopenia.

6. The method of claim 4, wherein the subject is at risk of thrombocytopenia.

7. The method of claim 1, wherein MkP cells are produced from CD34$^+$ HSC.

\* \* \* \* \*